(12) United States Patent
Caparso et al.

(10) Patent No.: US 11,691,010 B2
(45) Date of Patent: Jul. 4, 2023

(54) SYSTEMS AND METHODS FOR IMPROVING SLEEP DISORDERED BREATHING

(71) Applicant: XII Medical, Inc., Cleveland, OH (US)

(72) Inventors: Anthony V. Caparso, North Ridgeville, OH (US); Josh Nickols, Louisville, KY (US)

(73) Assignee: XII MEDICAL, INC., Union City, CA (US)

( * ) Notice: Subject to any disclaimer, the term of this patent is extended or adjusted under 35 U.S.C. 154(b) by 95 days.

(21) Appl. No.: 17/147,886

(22) Filed: Jan. 13, 2021

(65) Prior Publication Data

US 2022/0218988 A1  Jul. 14, 2022

(51) Int. Cl.

| | |
|---|---|
| *A61N 1/36* | (2006.01) |
| *A61N 1/05* | (2006.01) |
| *G16H 20/30* | (2018.01) |
| *G16H 40/67* | (2018.01) |
| *A61N 1/02* | (2006.01) |
| *A61N 1/372* | (2006.01) |
| *A61N 1/378* | (2006.01) |

(52) U.S. Cl.
CPC ........... *A61N 1/3601* (2013.01); *A61N 1/025* (2013.01); *A61N 1/0556* (2013.01); *A61N 1/36135* (2013.01); *A61N 1/3787* (2013.01); *A61N 1/37223* (2013.01); *A61N 1/37235* (2013.01); *A61N 1/37288* (2013.01); *G16H 20/30* (2018.01); *G16H 40/67* (2018.01)

(58) Field of Classification Search
CPC ................ A61N 1/3611; A61N 1/0556
See application file for complete search history.

(56) References Cited

U.S. PATENT DOCUMENTS

| | | |
|---|---|---|
| 910,774 A | 1/1909 | Beers |
| 4,990,160 A | 2/1991 | Terino |
| 5,591,216 A | 1/1997 | Testerman et al. |
| 5,609,621 A | 3/1997 | Bonner |
| 5,716,377 A | 2/1998 | Rise et al. |
| 5,877,466 A | 3/1999 | Bolongeat-Mobleu et al. |

(Continued)

FOREIGN PATENT DOCUMENTS

| | | |
|---|---|---|
| JP | 2013208182 A | 10/2013 |
| WO | 9219318 A1 | 11/1992 |

(Continued)

OTHER PUBLICATIONS

International Search Report and Written Opinion dated Apr. 22, 2022; International Application No. PCT/US2022/070101; 15 pages.

(Continued)

*Primary Examiner* — George R Evanisko
(74) *Attorney, Agent, or Firm* — Fortem IP LLP; Katrina Marcelo; Mary Fox

(57) ABSTRACT

A neuromodulation system is provided herein. The system can include a cuff electrode, an electronics package, which can be part of a neuromodulation device; an external controller; a sensor; and a computing device. The neuromodulation device can include an antenna including an upper and a lower coil electrically connected to each other in parallel. The computing device can execute a closed-loop algorithm based on physiological sensed data relating to sleep.

14 Claims, 10 Drawing Sheets

(56) References Cited

U.S. PATENT DOCUMENTS

| | | | |
|---|---|---|---|
| 5,988,171 | A | 11/1999 | Sohn et al. |
| 6,240,316 | B1 | 5/2001 | Richmond et al. |
| 6,587,725 | B1 | 7/2003 | Durand et al. |
| 6,770,022 | B2 | 8/2004 | Mechlenburg et al. |
| 7,660,632 | B2 | 2/2010 | Kirby et al. |
| 7,668,591 | B2 | 2/2010 | Lee et al. |
| 7,711,438 | B2 | 5/2010 | Lattner et al. |
| 7,885,713 | B2 | 2/2011 | Campbell et al. |
| 8,255,056 | B2 | 8/2012 | Tehrani |
| 8,498,712 | B2 | 7/2013 | Bolea et al. |
| 8,498,713 | B2 | 7/2013 | McClure et al. |
| 8,574,164 | B2 | 11/2013 | Mashiach |
| 8,577,464 | B2 | 11/2013 | Mashiach |
| 8,577,465 | B2 | 11/2013 | Mashiach |
| 8,577,466 | B2 | 11/2013 | Mashiach |
| 8,577,467 | B2 | 11/2013 | Mashiach et al. |
| 8,577,468 | B2 | 11/2013 | Mashiach et al. |
| 8,577,472 | B2 | 11/2013 | Mashiach et al. |
| 8,577,478 | B2 | 11/2013 | Mashiach et al. |
| 8,577,647 | B2 | 11/2013 | Farritor et al. |
| 8,585,617 | B2 | 11/2013 | Mashiach et al. |
| 8,588,941 | B2 | 11/2013 | Mashiach |
| 8,626,304 | B2 | 1/2014 | Bolea et al. |
| 8,644,957 | B2 | 2/2014 | Mashiach |
| 8,700,183 | B2 | 4/2014 | Mashiach |
| 8,718,776 | B2 | 5/2014 | Mashiach et al. |
| 8,744,589 | B2 | 6/2014 | Bolea et al. |
| 8,751,005 | B2 | 6/2014 | Meadows et al. |
| 8,798,773 | B2 | 8/2014 | Mashiach |
| 8,812,113 | B2 | 8/2014 | Mashiach |
| 8,812,135 | B2 | 8/2014 | Mashiach |
| 8,831,730 | B2 | 9/2014 | Mashiach et al. |
| 8,838,256 | B2 | 9/2014 | Mashiach et al. |
| 8,897,880 | B2 | 11/2014 | Mashiach |
| 8,897,895 | B2 | 11/2014 | Mashiach |
| 8,903,493 | B2 | 12/2014 | Mashiach et al. |
| 8,903,515 | B2 | 12/2014 | Mashiach |
| 8,948,871 | B2 | 2/2015 | Mashiach et al. |
| 8,958,893 | B2 | 2/2015 | Mashiach |
| 8,989,868 | B2 | 3/2015 | Mashiach et al. |
| 9,031,653 | B2 | 5/2015 | Mashiach |
| 9,031,654 | B2 | 5/2015 | Meadows et al. |
| 9,044,612 | B2 | 6/2015 | Mashiach et al. |
| 9,061,151 | B2 | 6/2015 | Mashiach et al. |
| 9,061,162 | B2 | 6/2015 | Mashiach et al. |
| 9,095,725 | B2 | 8/2015 | Mashiach |
| 9,101,774 | B2 | 8/2015 | Mashiach et al. |
| 9,155,899 | B2 | 10/2015 | Mashiach et al. |
| 9,186,511 | B2 * | 11/2015 | Bolea .................. A61F 5/566 |
| 9,220,907 | B2 | 12/2015 | Maschiach et al. |
| 9,220,908 | B2 | 12/2015 | Mashiach |
| 9,248,290 | B2 | 2/2016 | Mashiach |
| 9,248,291 | B2 | 2/2016 | Mashiach |
| 9,248,302 | B2 | 2/2016 | Mashiach et al. |
| 9,259,585 | B2 | 2/2016 | Vajha et al. |
| 9,302,093 | B2 | 4/2016 | Mashiach |
| 9,308,370 | B2 | 4/2016 | Lima et al. |
| 9,308,381 | B2 | 4/2016 | Mashiach et al. |
| 9,314,613 | B2 | 4/2016 | Mashiach |
| 9,314,641 | B2 | 4/2016 | Meadows et al. |
| 9,327,132 | B2 | 5/2016 | Mashiach |
| 9,339,651 | B2 | 5/2016 | Meadows et al. |
| 9,358,392 | B2 | 6/2016 | Mashiach |
| 9,370,657 | B2 | 6/2016 | Tehrani et al. |
| 9,393,435 | B2 | 7/2016 | Mashiach |
| 9,403,009 | B2 | 8/2016 | Mashiach |
| 9,403,025 | B2 | 8/2016 | Mashiach et al. |
| 9,409,013 | B2 | 8/2016 | Mashiach et al. |
| 9,415,215 | B2 | 8/2016 | Mashiach |
| 9,415,216 | B2 | 8/2016 | Mashiach |
| 9,421,372 | B2 | 8/2016 | Mashiach et al. |
| 9,463,318 | B2 | 10/2016 | Mashiach et al. |
| 9,486,628 | B2 | 11/2016 | Christopherson et al. |
| 9,757,560 | B2 | 9/2017 | Papay |
| 9,849,288 | B2 | 12/2017 | Meadows et al. |
| 9,950,166 | B2 | 4/2018 | Mashiach et al. |
| 10,029,098 | B2 | 7/2018 | Papay |
| 10,065,038 | B2 | 9/2018 | Papay |
| 10,105,538 | B2 | 10/2018 | Bolea et al. |
| 10,238,468 | B2 | 3/2019 | Forsell |
| 10,675,467 | B2 | 6/2020 | Papay |
| 11,291,842 | B2 * | 4/2022 | Caparso ............... A61N 1/0548 |
| 11,338,142 | B2 | 5/2022 | Papay |
| 11,351,377 | B2 | 6/2022 | Papay et al. |
| 11,420,061 | B2 | 8/2022 | Caparso et al. |
| 11,420,063 | B2 | 8/2022 | Caparso et al. |
| 2002/0010495 | A1 | 1/2002 | Tucker et al. |
| 2006/0224211 | A1 | 10/2006 | Durand et al. |
| 2007/0160274 | A1 | 7/2007 | Mashiach |
| 2007/0239230 | A1 | 10/2007 | Giftakis et al. |
| 2007/0263915 | A1 | 11/2007 | Mashiach |
| 2008/0039904 | A1 | 2/2008 | Beutler et al. |
| 2008/0260217 | A1 | 10/2008 | Mashiach |
| 2008/0260229 | A1 | 10/2008 | Mashiach |
| 2009/0082831 | A1 | 3/2009 | Paul et al. |
| 2009/0226057 | A1 | 9/2009 | Mashiach et al. |
| 2009/0270960 | A1 | 10/2009 | Zhao et al. |
| 2010/0094379 | A1 | 4/2010 | Meadows et al. |
| 2010/0179562 | A1 | 7/2010 | Linker et al. |
| 2010/0241195 | A1 | 9/2010 | Meadows et al. |
| 2010/0260217 | A1 | 10/2010 | Redford |
| 2010/0280568 | A1 | 11/2010 | Bulkes et al. |
| 2010/0292769 | A1 | 11/2010 | Brounstein et al. |
| 2011/0071606 | A1 | 3/2011 | Kast et al. |
| 2011/0093032 | A1 | 4/2011 | Boggs et al. |
| 2011/0093036 | A1 | 4/2011 | Mashiach |
| 2011/0125212 | A1 | 5/2011 | Tyler |
| 2011/0230702 | A1 | 9/2011 | Honour |
| 2012/0010532 | A1 | 1/2012 | Bolea et al. |
| 2013/0085537 | A1 | 4/2013 | Mashiach |
| 2013/0085558 | A1 | 4/2013 | Mashiach |
| 2013/0204097 | A1 | 8/2013 | Rondoni et al. |
| 2013/0289401 | A1 | 10/2013 | Colbaugh et al. |
| 2014/0031840 | A1 | 1/2014 | Mashiach |
| 2014/0031902 | A1 | 1/2014 | Mashiach et al. |
| 2014/0031903 | A1 | 1/2014 | Mashiach |
| 2014/0031904 | A1 | 1/2014 | Mashiach |
| 2014/0046221 | A1 | 2/2014 | Mashiach et al. |
| 2014/0052219 | A1 | 2/2014 | Mashiach et al. |
| 2014/0100642 | A1 | 4/2014 | Mashiach |
| 2014/0135868 | A1 | 5/2014 | Bashyam |
| 2014/0172061 | A1 | 6/2014 | Mashiach |
| 2014/0266933 | A1 | 9/2014 | Andersen et al. |
| 2014/0358026 | A1 | 12/2014 | Mashiach et al. |
| 2014/0358189 | A1 | 12/2014 | Mashiach et al. |
| 2014/0358196 | A1 | 12/2014 | Mashiach |
| 2014/0358197 | A1 | 12/2014 | Mashiach et al. |
| 2014/0371802 | A1 | 12/2014 | Mashiach et al. |
| 2014/0371817 | A1 | 12/2014 | Mashiach et al. |
| 2014/0379049 | A1 | 12/2014 | Mashiach et al. |
| 2015/0032177 | A1 | 1/2015 | Mashiach et al. |
| 2015/0073232 | A1 | 3/2015 | Ahmad et al. |
| 2015/0077308 | A1 | 3/2015 | Jeon et al. |
| 2015/0088025 | A1 | 3/2015 | Litvak et al. |
| 2015/0096167 | A1 | 4/2015 | Zhao et al. |
| 2015/0112402 | A1 | 4/2015 | Mashiach |
| 2015/0112416 | A1 | 4/2015 | Mashiach et al. |
| 2015/0142120 | A1 | 5/2015 | Papay |
| 2015/0224307 | A1 | 8/2015 | Bolea |
| 2015/0265221 | A1 | 9/2015 | Flanagan et al. |
| 2015/0283313 | A1 | 10/2015 | Huber |
| 2015/0290454 | A1 | 10/2015 | Tyler et al. |
| 2015/0290465 | A1 | 10/2015 | Mashiach |
| 2015/0343221 | A1 | 12/2015 | Mashiach |
| 2016/0094082 | A1 | 3/2016 | Ookawa et al. |
| 2016/0106976 | A1 | 4/2016 | Kucklick |
| 2016/0121121 | A1 | 5/2016 | Mashiach |
| 2016/0121122 | A1 | 5/2016 | Mashiach |
| 2016/0175587 | A1 | 6/2016 | Lima et al. |
| 2016/0184583 | A1 | 6/2016 | Meadows et al. |
| 2016/0235990 | A1 | 8/2016 | Mashiach |
| 2016/0346537 | A1 | 12/2016 | Mashiach |
| 2017/0087360 | A1 | 3/2017 | Scheiner |
| 2017/0106190 | A1 | 4/2017 | Papay |

(56) References Cited

U.S. PATENT DOCUMENTS

| | | |
|---|---|---|
| 2017/0143280 A1 | 5/2017 | Kent et al. |
| 2017/0274210 A1 | 9/2017 | Papay |
| 2017/0290699 A1 | 10/2017 | Radmand |
| 2017/0296815 A1 | 10/2017 | Papay |
| 2018/0015282 A1 | 1/2018 | Waner et al. |
| 2018/0028824 A1 | 2/2018 | Pivonka et al. |
| 2018/0117313 A1 | 5/2018 | Schmidt et al. |
| 2018/0191069 A1 | 7/2018 | Chen et al. |
| 2018/0200512 A1* | 7/2018 | Bolea .................. A61N 1/3611 |
| 2018/0221673 A1* | 8/2018 | Kuang ............... A61N 1/37229 |
| 2019/0151656 A1 | 5/2019 | Bolea et al. |
| 2019/0160282 A1 | 5/2019 | Dieken et al. |
| 2019/0247664 A1 | 8/2019 | Irazoqui et al. |
| 2020/0016401 A1 | 1/2020 | Papay et al. |
| 2020/0269044 A1 | 8/2020 | Papay |
| 2020/0346010 A1 | 11/2020 | Papay et al. |
| 2020/0346016 A1 | 11/2020 | Caparso et al. |
| 2020/0346017 A1 | 11/2020 | Caparso et al. |
| 2020/0346024 A1 | 11/2020 | Caparso et al. |
| 2021/0106824 A1 | 4/2021 | Caparso et al. |
| 2021/0128914 A1 | 5/2021 | Papay |
| 2022/0241588 A1 | 8/2022 | Caparso et al. |
| 2022/0266030 A1 | 8/2022 | Caparso et al. |
| 2022/0288390 A1 | 9/2022 | Papay et al. |
| 2022/0323752 A1 | 10/2022 | Papay |

FOREIGN PATENT DOCUMENTS

| | | |
|---|---|---|
| WO | 2005018737 A1 | 3/2005 |
| WO | 2007080579 A2 | 7/2007 |
| WO | 2007080579 A3 | 7/2007 |
| WO | 2007080580 A2 | 7/2007 |
| WO | 2007080580 A3 | 7/2007 |
| WO | 2008129545 A1 | 10/2008 |
| WO | 2009007896 A2 | 1/2009 |
| WO | 2009007896 A3 | 1/2009 |
| WO | 2009109971 A2 | 9/2009 |
| WO | 2009109971 A3 | 9/2009 |
| WO | 2009143560 A1 | 12/2009 |
| WO | 2010006218 A2 | 1/2010 |
| WO | 2011048590 A1 | 4/2011 |
| WO | 2011077433 A1 | 6/2011 |
| WO | 2013046032 A2 | 4/2013 |
| WO | 2013046032 A3 | 4/2013 |
| WO | 2013046035 A2 | 4/2013 |
| WO | 2013046035 A3 | 4/2013 |
| WO | 2013046038 A2 | 4/2013 |
| WO | 2013046038 A3 | 4/2013 |
| WO | 2013046039 A2 | 4/2013 |
| WO | 2013046039 A3 | 4/2013 |
| WO | 2013046040 A2 | 4/2013 |
| WO | 2013046040 A3 | 4/2013 |
| WO | 2013046042 A2 | 4/2013 |
| WO | 2013046042 A3 | 4/2013 |
| WO | 2013046043 A2 | 4/2013 |
| WO | 2013046043 A3 | 4/2013 |
| WO | 2013046044 A2 | 4/2013 |
| WO | 2013046044 A3 | 4/2013 |
| WO | 2013046048 A2 | 4/2013 |
| WO | 2013046048 A3 | 4/2013 |
| WO | 2013046049 A2 | 4/2013 |
| WO | 2013046049 A3 | 4/2013 |
| WO | 2013046053 A2 | 4/2013 |
| WO | 2013046053 A3 | 4/2013 |
| WO | 2013057594 A2 | 4/2013 |
| WO | 2013057594 A3 | 4/2013 |
| WO | 2013057597 A1 | 4/2013 |
| WO | 2013061164 A2 | 5/2013 |
| WO | 2013061164 A3 | 5/2013 |
| WO | 2013061169 A2 | 5/2013 |
| WO | 2013061169 A3 | 5/2013 |
| WO | 2013177621 A1 | 12/2013 |
| WO | 2014016684 A2 | 1/2014 |
| WO | 2014016684 A3 | 1/2014 |
| WO | 2014016686 A2 | 1/2014 |
| WO | 2014016686 A3 | 1/2014 |
| WO | 2014016687 A2 | 1/2014 |
| WO | 2014016687 A3 | 1/2014 |
| WO | 2014016688 A2 | 1/2014 |
| WO | 2014016688 A3 | 1/2014 |
| WO | 2014016691 A2 | 1/2014 |
| WO | 2014016691 A3 | 1/2014 |
| WO | 2014016692 A2 | 1/2014 |
| WO | 2014016692 A3 | 1/2014 |
| WO | 2014016693 A2 | 1/2014 |
| WO | 2014016693 A3 | 1/2014 |
| WO | 2014016694 A2 | 1/2014 |
| WO | 2014016694 A3 | 1/2014 |
| WO | 2014016697 A2 | 1/2014 |
| WO | 2014016697 A3 | 1/2014 |
| WO | 2014016700 A2 | 1/2014 |
| WO | 2014016700 A3 | 1/2014 |
| WO | 2014016701 A2 | 1/2014 |
| WO | 2014016701 A3 | 1/2014 |
| WO | 2014047310 A1 | 3/2014 |
| WO | 2014049448 A2 | 4/2014 |
| WO | 2014049448 A3 | 4/2014 |
| WO | 2014057361 A2 | 4/2014 |
| WO | 2014057361 A3 | 4/2014 |
| WO | 2014096969 A2 | 6/2014 |
| WO | 2014096969 A3 | 6/2014 |
| WO | 2014096971 A2 | 6/2014 |
| WO | 2014096973 A2 | 6/2014 |
| WO | 2014096973 A3 | 6/2014 |
| WO | 2014207576 A2 | 12/2014 |
| WO | 2014207576 A3 | 12/2014 |
| WO | 2015004540 A2 | 1/2015 |
| WO | 2015004540 A3 | 1/2015 |
| WO | 2015077283 A1 | 5/2015 |
| WO | 2015139053 A1 | 9/2015 |
| WO | 2020223723 A1 | 11/2020 |
| WO | 2020223740 A1 | 11/2020 |
| WO | 2021076188 A1 | 4/2021 |
| WO | 2022155632 A1 | 7/2022 |

OTHER PUBLICATIONS

International Search Report and Written Opinion dated Aug. 14, 2020, International Application No. PCT/US2020/031279, 19 pages.

International Search Report and Written Opinion dated Feb. 10, 2015, International Application No. PCT/US2014/066311, 8 pages.

International Search Report and Written Opinion dated Oct. 9, 2020, International Application No. PCTUS2020/031383, 13 pages.

International Search Report and Written Opinion dated Sep. 7, 2020, International Application No. PCT/US2020/031266, 8 pages.

International Search Report and Written Opinion dated Sep. 8, 2020, International Application No. PCT/US2020/031389, 9 pages.

Cienfuegos et al., "Mandible—Surgical approach", Intraocular—AO Surgery Reference, v1 .0 Dec. 1, 2008.

Cienfuegos et al., "Mandible—Surgical approach", Submental—AO Surgery Reference, v1 .0 Dec. 1, 2008 (Accessed Apr. 18, 2016).

Schwartz et al., "Electrical Stimulation of the Lingual Musculature in Obstructive Sleep Apnea", J Appl Physiol, vol. 81(2), Aug. 1996, 643-652.

Bailey, "Activities of human genioglossus motor units", Respiratory Physiology & Neurobiology 179:14-22, 2011.

Björninen, Toni, et al., "The Effect of Fabrication Method on Passive UHF RFID Tag Performance", International Journal of Antennas and Propagation, https://doi.org/10.1155/2009/920947, 2009, 8 pages.

* cited by examiner

SYSTEMS AND METHODS FOR IMPROVING SLEEP DISORDERED BREATHING

TECHNICAL FIELD

An electrical stimulation system for improving sleep disordered breathing is provided.

BACKGROUND

Obstructive sleep apnea (OSA) is the most common type of sleep apnea and is characterized by repeated episodes of complete or partial obstructions of the upper airway during sleep, despite the effort to breathe, and is usually associated with a reduction in blood oxygen saturation. Individuals with OSA are rarely aware of difficulty breathing, even upon awakening. It is often recognized as a problem by others who observe the individual during episodes or is suspected because of its effects on the body. OSA is commonly accompanied with snoring. OSA can be associated with symptoms during the daytime (e.g. excessive daytime sleepiness, decreased cognitive functions). Symptoms may be present for years or even decades without identification, during which time the individual may become conditioned to the daytime sleepiness and fatigue associated with significant levels of sleep disturbance. Individuals who generally sleep alone are often unaware of the condition, without a regular bed-partner to notice and make them aware of the signs.

The most widely used current therapeutic intervention for treating OSA is positive airway pressure whereby a breathing machine pumps a controlled stream of air through a mask worn over the nose, mouth, or both. The additional pressure holds open the relaxed muscles. There are several mechanisms for treating OSA with positive airway pressure therapy. The most common treatment involves the use of continuous positive airway pressure (CPAP) machines. CPAP machines are worn by the OSA patient at nighttime during sleep, with the patient wearing a mask connected by hose to an air pump that maintains positive airway pressure.

Neurostimulation therapy can be an alternative for patients who cannot use a continuous positive airway pressure device. One neurostimulation system senses respiration and deliver mild electrical stimulation to the hypoglossal nerve (HGN) in order to increase muscle tone at the back of the tongue so it will not collapse over the airway. The HGN innervates the tongue musculature. It provides motor control for the muscles of the tongue and helps with important voluntary and involuntary functions like swallowing, speaking, and mastication. Stimulating the HGN can restore the tone to key tongue muscles that, when relaxed, can lead to obstructive sleep apnea.

Conventional HGN neurostimulation systems utilize stimulation leads implanted in the patient's neck/throat, with electrodes touching, e.g., a cuff electrode that surrounds the HGN or in close proximity to the HGN. The leads are connected via wire to a pulse generator implanted under the skin in the patient's chest. From time-to-time, the pulse generator is surgically accessed for battery changes. The system includes a handheld patient controller to allow it to be switched on before sleep.

While HGN neurostimulation therapy has proven to be an effective treatment for OSA, the bulk of the conventional systems and the degree of invasiveness in implanting, using, and maintaining the system is undesirable.

SUMMARY

A neuromodulation system is provided herein. In an aspect, a neuromodulation system comprises a nerve cuff electrode comprising a cuff body having at least one stimulating electrical contact disposed thereon configured to deliver a stimulation signal to a target site. The system also includes a sensor configured to be implantable adjacent to an anterior lingual muscle and configured to record physiological data. The system further includes an antenna configured to produce an induced current in response to being disposed in an electromagnetic field and comprising an upper and a lower coil electrically connected to each other in parallel. The system further includes an electronics package comprising electrical components to control the application of a stimulation signal via the at least one stimulating electrical contact of the nerve cuff electrode. An external controller is provided which comprises a control unit and a power mat that supports one or more power transmission coils that are excitable to produce an electromagnetic field for inducing electrical current in the antenna to power the electronics package. The system also includes a computing device comprising a non-transitory memory storing instructions and a processor to access the non-transitory memory and execute the instructions. Such instructions include monitoring the physiological data recorded by the sensor, identifying a trigger within the physiological data, wherein the trigger is identified as a biomarker for a physiological condition related to sleep, and applying a rule-based classification to the trigger to determine whether one or more parameters of the stimulation signal should be altered based on the biomarker and altering the one or more parameters of the stimulation signal in response to the biomarker. In certain aspects, the sensors can comprise a plurality of sensors disposed on the lead body of a neuromodulation lead.

DETAILED DESCRIPTION

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. As used herein, "stimulate" or "modulate" in the context of neuromodulation includes stimulating or inhibiting neural activity. A "patient" as described herein includes a mammal, such as a human being. By "improving," the patient's medical disorder is better after therapy than before therapy. As used herein, the terms, "inferior," "superior," "cranial," and caudal refer to anatomical planes and directions when the patient is in a standard anatomical position. Similarly, the terms "left" and "right" refer to the position of elements that correspond to the left and right side of a patient's body in a standard anatomical position. By "integral" or "integrated" is meant that the described components are fabricated as one piece or multiple pieces affixed during manufacturing or the described components are otherwise not separable using a normal amount of force without damaging the integrity (i.e. tearing) of either of the components. As used herein, a "neuromodulation device" is a device that is not implanted in the oral cavity of a patient.

The present disclosure relates to an implantable electrical stimulation or neuromodulation system, which can be used to provide a variety of electrical therapies, including neuromodulation therapies such as nerve and/or muscle stimulation. Stimulation can induce excitatory or inhibitory neural or muscular activity. Such therapies can be used at various suitable sites within a patient's anatomy. In one example implementation, the system can be used to treat sleep disordered breathing (SDB) including obstructive sleep apnea (OSA) via neuromodulation of the hypoglossal nerve (HGN) and/or other nerves that innervate anterior lingual muscles such as protruser muscles; other muscles of the tongue; and/or pharyngeal muscles, such as the posterior pharyngeal walls.

Figure 1:
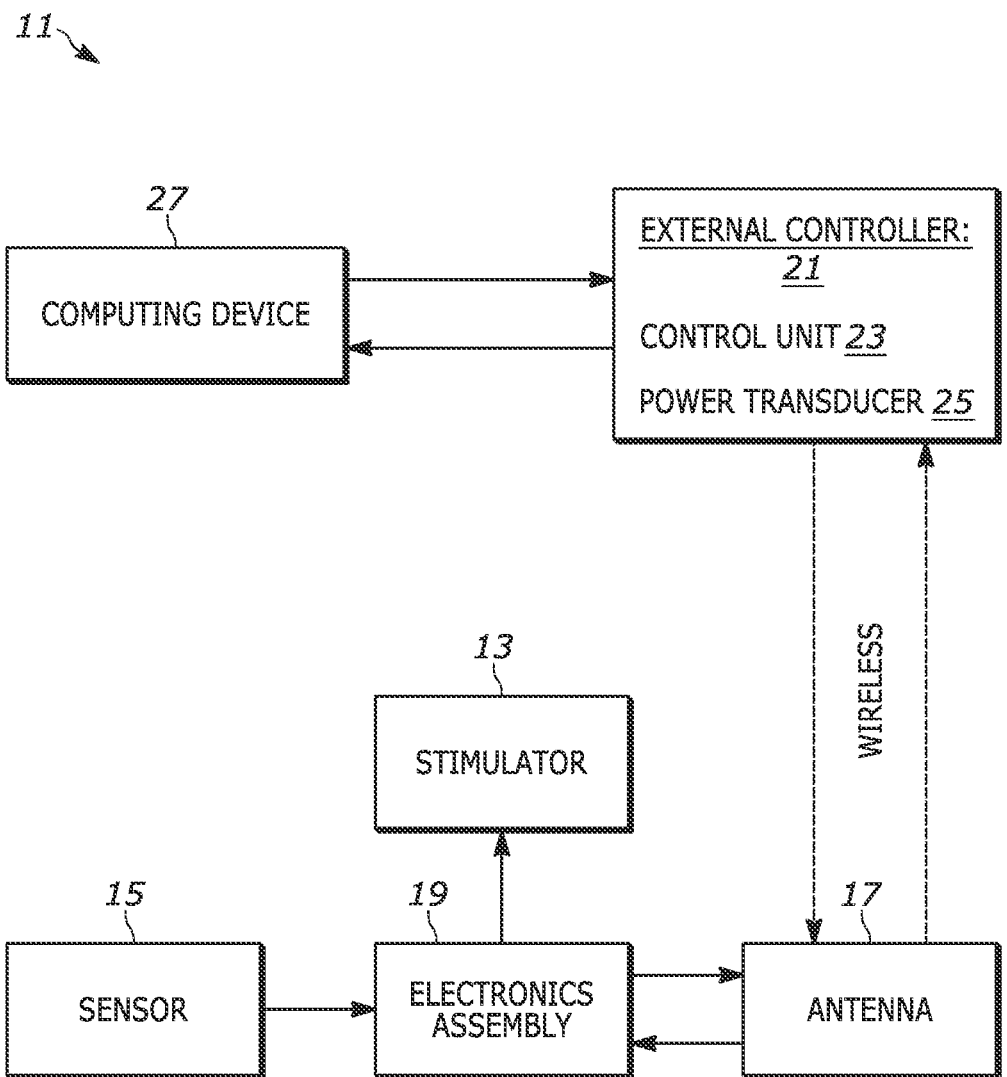
FIG. 1 is a diagram illustrating an example configuration of a neuromodulation system according to an aspect of the present disclosure.

Referring to FIG. 1, in an embodiment, a neuromodulation system 11 is provided that include a stimulator 13, a sensor 15, an antenna 17, an electronics assembly 19, an external controller 21, and an internal computing device 27.

As described in more detail below, stimulator 13 can have a stimulating electrical contact disposed thereon configured to deliver a stimulation signal to a stimulation site. The neuromodulation system can include a plurality of stimulators and a plurality of stimulating electrical contacts disposed on each stimulator. Sensor 15 can have a sensing contact disposed thereon configured to be implantable adjacent to a sensing site and configured to record physiological signals. The neuromodulation system can comprise a plurality of sensors and a plurality of sensing contacts on each sensor. For example, the neuromodulation system can comprise a first cuff lead having a cuff body comprising a plurality of stimulating electrical contacts disposed thereon and a second cuff lead having a cuff body comprising a plurality of stimulating electrical contacts disposed thereon. The sensor can comprise a sensing lead having a lead body comprising a plurality of sensing contacts disposed thereon. The first cuff lead can have a cuff body sized and configured to at least partially wrap around a first nerve branch site comprising a hypoglossal nerve branch distal to the hypoglossal nerve trunk. The second cuff lead can have a cuff body sized and configured to at least partially wrap around a second nerve branch site proximal to the first nerve branch site. In certain aspects, the stimulator is a stimulating lead and the sensor is a sensing lead. Both leads can be operably coupled to the electronics assembly and the electronics assembly can be operably coupled to the antenna. The antenna can be configured to supply electrical current to the electronics assembly to power the electronics assembly. The stimulating lead, the sensing lead, the electronics assembly, and the antenna can be parts of a single neuromodulation device. The antenna can be located at a proximal end of the neuromodulation device, the electronics assembly can be operably coupled to the antenna, and the stimulating lead and sensing lead can extend distally from the electronics assembly. In certain aspects, the sensor can be a sensing lead comprising a lead body with a right portion, a left portion, and an intermediate portion defining an apex of the lead body. A left set of sensors can be disposed on the left portion of the lead body and a right set of sensors can be disposed on the right portion of the lead body. The lead body can be biased towards an omega shape when the neuromodulation lead is fully deployed and the intermediate portion of the lead body can be biased towards an inferior position relative to the left and right sensor sets when the neuromodulation lead is fully deployed.

Antenna 17 can be configured to produce an induced current in response to being disposed in an electromagnetic field. The antenna can comprise an upper and a lower coil electrically connected to each other in parallel.

Electronics assembly 19 can comprise electrical components to control the application of the stimulation signal via the stimulating electrical contact of the stimulator and sensing of the physiological signal by the sensor. External controller 21 can comprise control unit 23 and power transducer 25 that supports a power transmission coil that is excitable to produce an electromagnetic field for inducing electrical current in the antenna to power the electronics assembly. The power transducer can be a mat as described in more detail below.

Internal computing device 27 can comprise a non-transitory memory storing instructions and a processor to access the non-transitory memory. The processor can execute the instructions to at least monitor the physiological signals recorded by the sensor and identify a trigger within the physiological signals, where the trigger is identified as a biomarker for a condition related to sleep. In certain aspects, the trigger indicates a change in phasic and/or tonic genioglossus muscle activity during respiration. The processor can further execute instructions to apply a rule-based classification to the trigger to determine whether one or more parameters of the stimulation signal should be altered based on the biomarker and to alter the one or more parameters of the stimulation signal in response to the biomarker. In certain aspects, the rule-based classification is adaptive. The initial rules of an algorithm used by the rule-based classification can be determined based on historical values for a population, historical values for a patient, and/or patient derived values.

In certain aspects, a method of improving sleep disordered breathing in a patient suffering therefrom is provided. Such a method can comprise obtaining a neuromodulation system as described above and herein. The method can further include placing the stimulator on a stimulation target site comprising a trigeminal nerve or a branch thereof, a facial nerve or a branch thereof, a glossopharyngeal nerve or a branch thereof, a vagus nerve or a branch thereof, a hypoglossal nerve trunk, a lateral branch of the hypoglossal nerve, a medial branch of the hypoglossal nerve, or suitable combinations thereof. A sensor can be placed on a sensing target site comprising a trigeminal nerve or a branch thereof, a facial nerve or a branch thereof, a glossopharyngeal nerve or a branch thereof, a vagus nerve or a branch thereof, a hypoglossal nerve trunk, a lateral branch of the hypoglossal nerve, a medial branch of the hypoglossal nerve, a tongue muscle, an upper airway muscle, a pharyngeal muscle, a cricopharyngeus muscle, or suitable combinations thereof. The method can further include activating the sensor to sense physiological signals from the sensing target site and activating the stimulator to stimulate the stimulation target site based on the sensed physiological signals to improve the patient's sleep disordered breathing.

Electrical Neuromodulation Device System

Referring to FIG. 1, the system 10 can include an implantable neuromodulation device 20 and external controller 100. Controller 100 can power neuromodulation device 20 through electromagnetic induction. Neuromodulation device 20 can include power receiver 30 with antenna 32. Electrical current can be induced in antenna 32 when it is positioned above power mat 112 of controller 100, in an electric field produced by power transmit antenna 112. Antennas 112 and 32 can also facilitate communication between controller 100 and neuromodulation device 20, respectively. This power/communication link between neuromodulation device 20 and controller 100 is shown generally by the arrow 70 in FIG. 1.

System 10 can also include a user interface 200 in the form of a computer platform 202 running a custom application that enables communication with controller 100 wirelessly, as indicated generally by arrow 204. This can be done, for example, using Bluetooth or WiFi radio communication. In the example configuration of FIG. 1, computer platform 202 is a smartphone. The type of computer platform 202 could, however, vary. For example, the computer platform 202 can be a physician or patient platform. Each platform 202 can have an application or "app" installed thereon that is user specific, i.e., a patient app or a physician app. The physician platform would have the physician app installed, and the patient platform would have the patient app installed. The patient app can allow the patient to execute certain commands necessary for controlling operation of neurostimulation device 20, such as, for example, start/stop therapy, increase/decrease stimulation power or intensity, and select a stimulation program. In addition to the controls afforded the patient, the physician app can also allow the physician to modify stimulation settings, such as pulse settings (patterns, duration, waveforms, etc.), stimulation frequency, amplitude settings, and electrode configurations, closed-loop and open loop control settings and tuning parameters for the embedded software that controls therapy delivery during use.

As indicated generally by arrow 206, computer platform 202 can be connected (e.g., WiFi and/or LTE) to internet/cloud 208, which facilitates communication 214 with remote or cloud-based server 216. This can allow for the transfer of data between server 216 and computer platform 202 via internet 208. Additionally, controller 100 itself can also be internet connected (e.g., WiFi), as shown at 210. This can also allow for the transfer of data between controller 100 and server 216 via internet 208.

System Communication

As shown in FIG. 1 and described above, system 10 can be configured to provide various communication paths between the system components. For example, computer platform 202 being connected to controller 100 (see 204) and to internet 208 (see 206) can facilitate a communication path from remote server 216 (see 214) to neuromodulation device 20 itself (see 70). A communication path between server 216 and neuromodulation device 20 can also be established via WiFi link 210 of controller 100.

Additionally, recognizing that the physician may be remote from the patient, a physician communication path can be established via the internet connection 206 of the remotely located physician platform 202. Through this connection, remote physician platform 202 can communicate with server 216 through internet connection 206. Remote physician platform 202 can also communicate with controller 100, either via internet connection 210 (when enabled) or through patient controller 202.

In addition to facilitating local control of system 10, e,g, controller 100 and neuromodulation device 20, the various communication paths described above can also enable:

Distributing from server 216 software/firmware updates for the computer platform 202, controller 100, and/or neuromodulation device 20.

Downloading from server 216 therapy settings/parameters to be implemented by computer platform 202, controller 100, and/or neuromodulation device 20.

Facilitating therapy setting/parameter adjustments/algorithm adjustments by a remotely located physician.

Uploading data recorded during therapy sessions.

Maintaining coherency in the settings/parameters by distributing changes and adjustments throughout the system components.

System Operation Overview

The therapeutic approach implemented with system 10 can involve implanting only neuromodulation device 20, leaving controller 100 as an external component to be used only during the application of therapy. To facilitate this, neuromodulation device 20 can be configured to be powered by controller 100 through electromagnetic induction. In operation, power mat 110, operated by control unit 120, can be positioned external to the patient in the vicinity of neuromodulation device 20 to position transmitting antenna 112 of the controller, located in the mat, close to receiving antenna 32 of the neuromodulation device. In the implementation where the system 10 is used to treat OSA, the power mat 110 can be positioned on or sufficiently near the sleeping surface while the patient sleeps to maintain the position of the receiving antenna 32 within the target volume of the electromagnetic field generated by the power antenna 112.

Through this approach, system 10 can deliver therapy to improve SDB such as OSA, for example, by stimulating the HGN, for example, through a shorter, less invasive procedure. The elimination of an on-board, implanted power source in favor of an inductive power scheme can eliminate the need for batteries and the associated battery changes over the patient's life.

Additionally, neuromodulation device 20 can implement electromyography (EMG) electrodes for sensing neuromuscular responses to physiological needs of the patient during sleep. Such sensing electrodes can continuously monitor physiological intrinsic EMG signals from the anterior lingual musculature. For instance, EMG sensing electrodes can be configured to detect neuromuscular responses from the genioglossus muscle, which is innervated by the HGN or to detect neuromuscular responses from other anterior lingual muscles and other muscles of the tongue.

Controller 100 can use transmitting antenna 112 for multiple purposes, for example: 1) to provide power to neuromodulation device 20 during therapy sessions, and 2) to communicate with the neuromodulation device. This communication can, for example, include programming, e.g., uploading software/firmware revisions to neuromodulation device 20, changing/adjusting stimulation settings and/or parameters, and adjusting parameters of control algorithms. Controller 100 can receive the programming, software/firmware, and settings/parameters through any of the communication paths described above, e.g., from user interface 200 or through direct WiFi internet connection, when available. The communication paths can also be used to download data from neuromodulation device 20, such as measured data regarding completed stimulation therapy sessions, to the controller 100. The controller 100 can transmit the downloaded data to the user interface 200, which can send/upload the data to server 216 via internet 208.

In operation, sensed EMG responses from the genioglossus muscle, for example, can allow closed-loop operation of the neuromodulation device 20 while eliminating the need for a chest lead. Operating in closed-loop, the neuromodulation device 20 can maintain stimulation synchronized with respiration, for example, while preserving the ability to detect and account for momentary obstruction. The neuromodulation device 20 can also detect and respond to snoring, for example.

To facilitate real-time, closed-loop control, a control algorithm can be implemented locally on neuromodulation device 20. This can be achieved, for example, by programming a control algorithm on an application-specific integrated circuit (ASIC) component of neuromodulation device 20 (see below for the description of the neuromodulation device electronics).

Operating in real-time, neuromodulation device 20 can record data related to the stimulation session including, for example, stimulation settings, EMG responses, respiration, sleep state including different stages of REM and non-REM sleep, etc. For example, changes in phasic and tonic EMG activity of genioglossus muscle during inspiration can serve as a trigger for stimulation or changes in stimulation can be made based on changes in phasic and tonic EMG activity of the genioglossus muscle during inspiration or during different sleep stages. After the sleep session, this recorded data can be uploaded to user interface 200 and to server 216. Also, the patient can be queried to use the interface 200 to log data regarding their perceived quality of sleep, which can also be uploaded to the server 216. Offline, the server 216 can execute a software application to evaluate the recorded data to determine whether settings and control parameters can be adjusted to further optimize the stimulation therapy. The software application can, for example, include artificial intelligence (AI) models that, learn from recorded therapy sessions, how certain adjustments affect the therapeutic outcome for the patient. In this manner, through AI learning, the model can provide patient-specific optimized therapy.

Figure 9A:
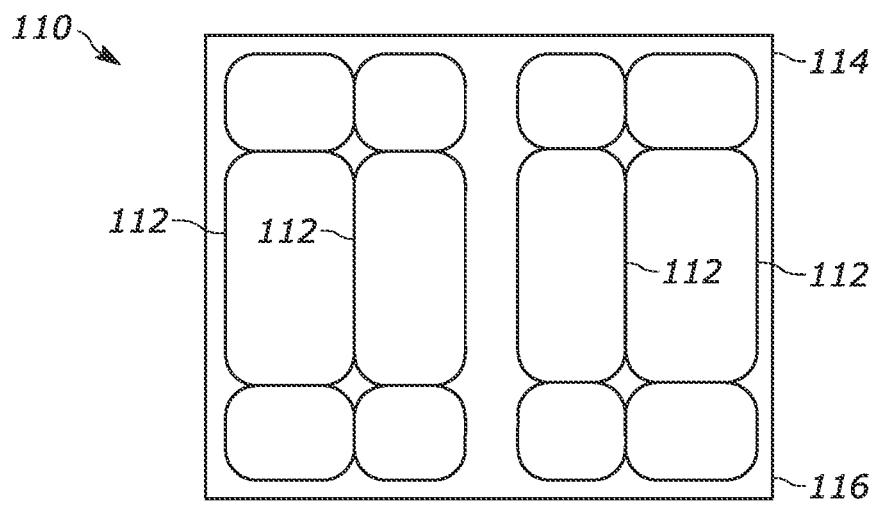
FIGS. 9A-9C are schematic illustrations depicting exemplary configurations of a power mat portion of a neuromodulation system according to an aspect of the present disclosure.
Figure 9B:
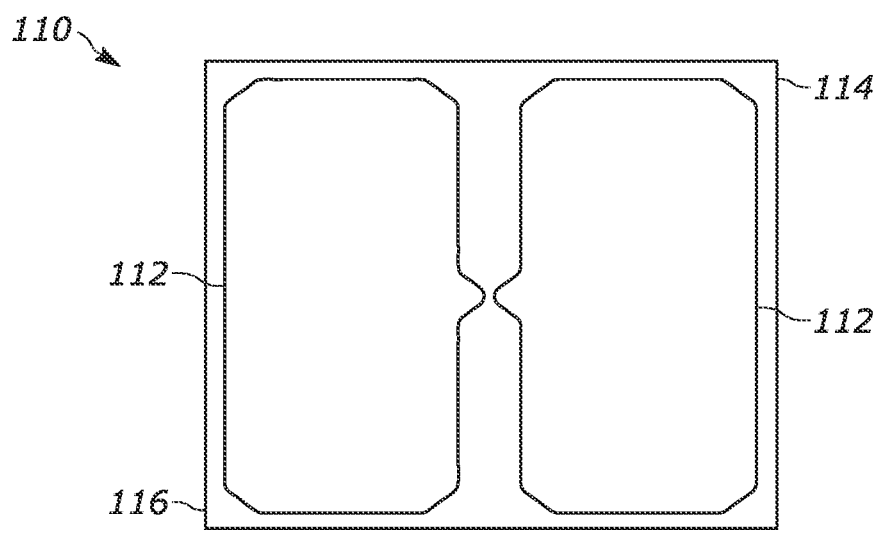
Figure 9C:
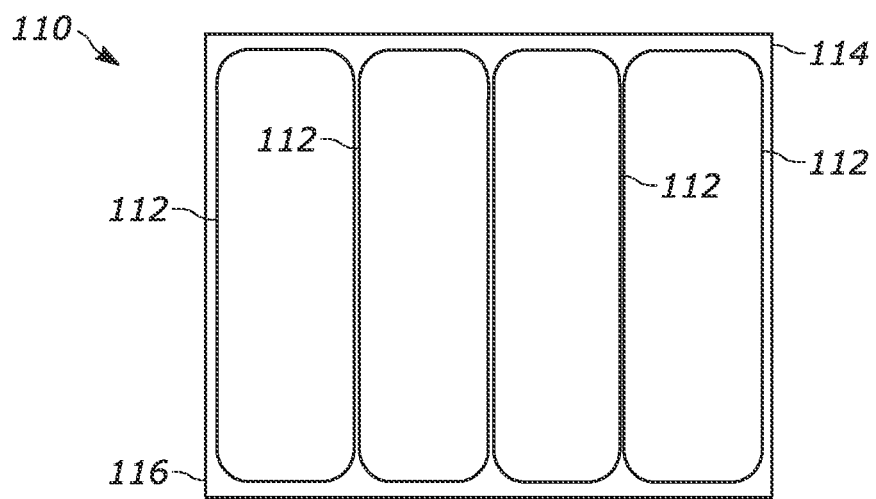

With reference to FIG. 9, system 300 can be implemented within the system 10 and/or the neuromodulation device 20 to provide stimulation to improve SDB according to open-loop control or closed-loop control. The system can include one or more sensors 302 (which can be implanted and/or external), a computing device 304 (which can be implanted and/or external, and may be part of another device like the controller), and one or more electrodes 306 (which can be implanted and/or external). The one or more sensors can be configured to record/detect physiological data (e.g. data originating from the patient's body) over time including changes therein. Exemplary physiological data can include phasic contraction of anterior lingual musculature, such as phasic genioglossus muscle contraction, underlying tonic activity of anterior lingual musculature, such as tonic activity of the genioglossus muscle, and combinations thereof. Phasic contraction of the genioglossus muscle can be indicative of inspiration, particularly the phasic activity that is layered within the underlying tonic tone of the genioglossus muscle. Changes in physiological data include changes in phasic contraction of anterior lingual musculature, such as phasic genioglossus muscle contraction, changes in underlying tonic activity of anterior lingual musculature, such as changes in tonic activity of the genioglossus muscle, and combinations thereof. For example, EMG signal changes can include changes in the frequency, amplitude, spike rate, or other features within the EMG signal. In particular, changes in phasic contraction of the genioglossus muscle can indicate a respiration or inspiration change and can be used to as a trigger for stimulation. Such physiological data and changes therein can be identified in recorded EMG signals, such as during different phases of respiration including inspiration. As such, one or more sensors 302 can include EMG sensors. The one or more sensors 302 can also include, for example, wireless or tethered sensors that measure, body temperature, movement, breath sounds (e.g. audio sensors), heart rate, pulse oximetry, eye motion, etc.

The computing device 304 can be configured to provide open-loop control and/or closed-loop stimulation to configure parameters for a stimulation. In other words, with respect to closed-loop stimulation, the computing device can be configured to track the patient's respiration (such as each breath of the patient) and stimulation can be applied during inspiration, for example. However, with respect to open-loop stimulation, stimulation can be applying without tracking specific physiological data, such as respiration or inspiration. However, even under such an "open loop" scenario, the computing device can still adjust stimulation and record data, to act on such information. For example, one way the computing device can act upon such information is that the computing device can configure parameters for stimulation to apply stimulation in an open loop fashion but can monitor the patient's respiration to know when to revert to applying stimulation on a breath to breath, close-loop fashion such that the system is always working in a close looped algorithm to assess data. Accordingly, adjustments to stimulation may be based on an input to the computing device 304, which may be based on one or more trends in physiological data recorded by the one or more sensors 302 over time. Treatment parameters of the system may be automatically adjusted in response to the physiological data. The physiological data can be stored over time and examined to change the treatment parameters; for example, the treatment data can be examined in real time to make a real time change to the treatment parameters.

Figure 10:
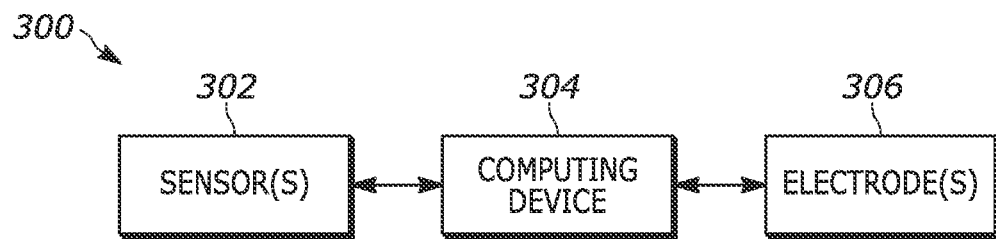
FIG. 10 is a block diagram of an example system that can provide neural stimulation according to a closed loop algorithm to treat sleep disordered breathing (SDB), which can be part of the system of FIG. 1.

An example of the computing device 304 programmed to implement the closed-loop scenario is shown in FIG. 10. The computing device 304 can include a memory 422 (e.g., a non-transitory memory), a processor 424 (e.g., an integrated circuit, such as an application specific integrated circuit (ASIC)), or an ASIC comprising both a memory and a processor. For example, the memory 422 can be a computer-usable or computer-readable medium that can contain or store the machine-readable instructions (which are, for example, a program) for use by or in connection with the instruction or execution of a system, apparatus or device (like the computing device 304) by the processor 424. The computer-usable or computer-readable medium can be, for example but not limited to, random access memory (RAM) including static or dynamic RAM, read-only memory (ROM), flash memory, an Erasable Programmable Read Only Memory (EPROM), floating point memory, or combination thereof including combinations thereof on the same ASIC. The processor 424, for example, can include one or more processing cores, processing units, or the like. The memory 422 can store machine readable instructions, while the processor 424 can access the memory 422 and execute the machine readable instructions (e.g., which can include one or more programs) and cause the computing device 304 to perform operations of a monitoring component 426, an identification component 427, and/or a classification component 428. The processor 424 can interpret the physiological information coming from the sensors, including decoding data, analyzing data, recognizing patterns, etc.

The monitoring component 426 can monitor the physiological data recorded by the sensor(s) 302. The identification component 427 can identify a trigger within the physiological data (e.g., related to respiration). For example, the monitoring component can monitor EMG waveform characteristics like spike rate, amplitude, and frequency, as well as phasic activity and tonic activity (again monitoring for changes in amplitude, frequency or other parameters of the EMG). The identification component can identify the trigger during such monitoring (e.g. a characteristic change in the EMG waveform). In one example, the trigger can be an associated change in the EMG, such as short term contraction of the genioglossus muscle indicating phasic genioglossus muscle activity or longer term changes in genioglossus muscle activity indicating a change in underlying tonic tone of the genioglossus muscle seen over one or more parts or repetitions of the physiological data. The trigger can be identified as a biomarker for a condition related to sleep, such as a change in at least one parameter physiological data. In some instances, the biomarker can be inspiration. In other instances, the biomarker can be a body position. In other instances, the biomarker can be a stage in a sleep cycle (e.g., awake, non-REM sleep—stage 1 light sleep, stage 2 light sleep, stage 3 deep sleep, REM sleep, etc.). In some instances, motion detection and/or other biomarkers can be used to automatically turn the therapy on only once the patient has fallen asleep and to determine the parameters of stimulation to optimally maintain airway patency throughout the night (including adapting stimulation based on sleep stage and body position) without causing unnecessary discomfort or leading to arousal events to increase patient comfort and adherence to therapy. Stimulation can be ramped up as the patient moves from light to deep sleep or ramped during each stimulation phase such that the first pulse in a pulse train has less amplitude and/or pulse width than the last pulse in the pulse train. In some instances, stimulation will automatically shut off if the patient wakes up and re-initiate as they fall back to sleep.

The awake stage of the sleep cycle refers to a relaxation stage when the subject is first lying in bed or lying in bed trying to fall asleep again. Non-REM sleep has three stages and is a stage of sleep without rapid eye movement. The REM stage includes REM sleep, where eyes move rapidly from side to side behind closed eyelids, breathing becomes faster and irregular, heart rate and blood pressure increase to near waking levels, and arm and leg muscles become temporarily paralyzed.

Non-REM stage 1 refers to the changeover from wakefulness to sleep (lasting several minutes). During non-REM stage 1, a subject's heartbeat, breathing, and eye movements slow and muscles relax with occasional twitches. Non-REM stage 2, the longest of all the stages, is a period of light sleep before entering deeper sleep, where heartbeat and breathing slow, muscles relax even further, body temperature drops and eye movement stops. Non-REM stage 3 refers to the period of deep sleep needed to feel refreshed in the morning, where heartbeat and breathing slow to their lowest levels during sleep, muscles are relaxed, and it may be difficult to awaken.

The sleep state can be determined, for example, based on information in the physiological data (e.g., tonic genioglossus muscle activity as indicated on an EMG). Once the sleep state is recognized, the goal is to apply therapy in such a way to minimize patient discomfort and to also minimize potential stimulation related arousal events. This may include, reducing the amplitude of stimulation during stage 1 and stage 2 sleep, and increase amplitude during stage 3 and REM. This may also include ramping therapy over a longer period of time, meaning from zero to programmed output over a longer time period, during stage 1 and 2 sleep vs. stage 3 and REM sleep or ramping therapy within each pulse train, when applied during inspiration for example.

For example, if certain EMG activity is detected, like phasic changes in EMG activity that is indicative of inspiration during any phase of sleep, the system may deliver stimulation during the respiratory period of inspiration. The system can apply stimulation to the hypoglossal nerve, for example, using a particular set of electrodes, waveform, pulse width, frequency, intra-pulse interval and pulse ramp rate that provide therapeutic airway patency during inspiration. The system can stop stimulation during the exhalation period and can continue to monitor the physiological EMG, from the genioglossus muscle for example, throughout the inspiratory and exhalation periods of each breath. The system can adjust the stimulation parameters and/or the electrodes selected for stimulation as necessary to optimize the stimulation to provide the optimal airway patency, based on additional biomarkers including, sleep state, body position, or the like. The closed loop algorithms embedded within the neuromodulation device or neuromodulation lead can continuously monitor and adjust therapy based on the physiological data and triggers and use rule based classification to determine when, how and for what period of time, to apply and adjust stimulation to provide optimal airway patency during sleep.

For example, if certain EMG activity, like tonic and phasic EMG activity drops or ceases during REM, the system may deliver a stimulation periodically based on predetermined physician programmed parameters, the system may rely on previous known patient specific parameters to apply stimulation, or the system may use a default periodic stimulation that is applied throughout REM sleep. The system can also monitor EMG through the REM period to determine when to stop using the periodic stimulation and when to re-initiate applying stimulation during each inspiratory event.

In some instances, the system may not turn on stimulation immediately when the neuromodulation device is within the field from the transmit coil. In this case, the system can turn on and monitor an EMG signal, e.g., detecting tonic and phasic muscle activity, to understand the sleep stage. Once the system has determined the patient is sleeping, entering stage 1 of sleep or stage 2 of sleep, the system 10 can start to provide therapy in a physiological manner, e.g., starting to apply small amount of stimulation using a stimulus ramp during each stimulation period, such that unnecessary arousal events or discomfort is not caused during initial phases of sleep. In this configuration, the EMG may be monitored for several minutes or several hours to determine the state before the system initiates therapy. Many individuals with OSA also suffer from insomnia, in which the individual has trouble falling asleep, and in this case, a negative feedback loop can cause the patient additional anxiety, such that they are fearful that the therapy will turn on prior to when they fall asleep and as such are not relaxed enough to fall asleep. This can cause the individual to turn off therapy, or over time discontinue use of the therapy. A "smart" system that is able to recognize when patients are asleep and apply therapy such that it is physiological will increase therapy adherence and efficacy. Once the system recognizes non-REM stage 1, for example, the system can start to recognize non-REM stage 2, non-REM stage 3, REM sleep, or the like.

For example, the ASIC (an example of processor 424) can be configured to control a custom algorithm, which can control the therapy application. For example, the ASIC can be configured to run embedded digital logic that uses information gathered by an EMG sensor to decide when, for how long, and at what stimulation parameters to stimulate to provide the optimal therapy to the subject to control the volume of air capable of flowing through the upper airway, also known as airway patency. The embedded digital logic can sense EMG activity, which can be known to the algorithm to correspond with respiration, more specifically to inspiration and exhalation. The algorithm can decode the EMG activity to trigger stimulation of the anterior musculature and/or the hypoglossal nerve (including distal branches thereof) bilaterally, for example, to open the airway, such that the therapy is linked to each respiration, each inspiration and each exhalation, for example. Therapy can thus be provided during each breath, specifically during inspiration, for example, all by using embedded correlative knowledge of the EMG features that correspond to respiration. The embedded logic can include knowledge of EMG features that are specific to body position, chin position, sleep state (e.g. REM, non-REM), movement, and other physiological parameters that can elucidate and optimize therapy. The algorithm can use adaptive learning to learn individual subject specific EMG features that correlate to the above physiological states during sleep to provide additional optimization that is subject specific. The adaptive learning can be done manually with physician input or may be done completely within the algorithm based on pre-determined limits and knowledge or can be done with the cloud database and the additional adaptive learning that the cloud software can use to analyze the data from each patient and each sleep session. The algorithm, while still based on respiratory information sensed through the EMG sensor, can also have different modes. In one mode, the algorithm can be running and can provide therapy breath to breath, specifically during inspiration; in another mode, the algorithm can be learning, looking for inputs from the EMG and also from the user (e.g. patient, physician, etc.); in another mode, the algorithm can provide more continuous control of the airway, providing periodic stimulation that can be sustained for periods of time. In another mode, the algorithm can be sensing EMG information, but not providing therapy breath to breath, instead waiting until a forthcoming collapse of the airway has been identified and reacting by providing therapy that prevents the collapse from occurring. The EMG information can include, the amplitude of the EMG, the frequency components of the EMG, spike sensing, envelope sensing, and other features that can be taken directly from the EMG signal to control the algorithm and provide biomarkers for respiration and for collapse of the airway. It is understood, that the algorithm may use any or all of these features throughout the sleep period and can switch between modes based on the EMG activity as sensed by the EMG sensor or the system may be hard programmed to only run one algorithm.

The system can apply therapy in a manner that is not causing discomfort and/or arousal events in the patient. As the patient moves through the stages over the course of the entire night, the system can continuously adapt to the sleep stage (and/or patient need). For example, the largest need for stimulation can be during deep sleep (non-REM stage 3) and REM, where discomfort and arousal are unlikely, so the system can apply more stimulation, since arousal and discomfort are unlikely during these stages. The amount of time the patient is spending in each stage of sleep can also be tracked, which is very useful for tracking outcomes, as most OSA patient do not enter into deep sleep often due to arousals.

The classification component 428 can apply a rule-based classification to the trigger to determine whether one or more stimulation parameters applied by one or more of the stimulating electrodes should be altered based on a biomarker related to sleep. As stated above, biomarkers include respiration phase (such as inspiration including periods within inspiration), sleep stage during one or more sleep cycles, and/or body position during sleep as indicated by an EMG or other sensor or sensed activity. Stimulation parameters, as stated above, include, for example, pulse width, amplitude, frequency, waveform shape, electrode position/configuration, or the like). Initial rules of the rule-based classification used by the algorithm can be set for the patient and/or set based on historical values for a population, historical values for a patient, and/or patient derived values. Subsequent rules of the algorithm can be learned and/or updated and/or personalized based on an artificial intelligence learning process.

Feedback related to the stimulation (e.g., after it is delivered) can be given to the computing device 304. The computing device 304 can receive the feedback and may change one or more stimulation parameters.

An example closed-loop control scenario involves the one or more sensors 302 (implanted adjacent to an anterior lingual muscle, such as the genioglossus muscle) that can detect/record physiological data over time. The physiological data can include EMG data from the musculature of the anterior airway, which can include characteristic signals that correlate to respiration, but also can correlate to sleep position, sleep state, and/or other physiological characteristics important for the treatment of SDB. The computing device 304 can monitor the physiological data recorded by the one or more sensors 302 to identify a trigger within the physiological data. The trigger can be identified as a biomarker for a condition related to sleep (e.g., inspiration). A rule-based classification can be applied to the trigger to determine whether one or more parameters of the stimulation (e.g., delivered by one or more electrodes 306 or electrode contacts to the hypoglossal nerves or other nerves) should be altered based on the biomarker.

Changes in voltages on the transmit receptor can be sensed, as well as on the power receiver and resulting changes in impedances to determine the position and movement of the power receptor within the magnetic field. In this aspect, the changes in voltage and impedance between the two coils of the power antenna can provide additional information to the system to inform the close loop algorithm and to inform additional refinement to the therapy. This type of position sensor may have additional usages beyond therapy optimization as it may provide additional data about sleep quality over time, as well as health related information. In addition, the impedance data between the coils can be correlated with activity, which can be used to also track wake vs. sleep cycles. These data along with EMG data, e.g. tonic EMG activity from the genioglossus muscle, can be used together to understand and learn wake vs. sleep throughout the period spent attempting to sleep (e.g., when the power receive coil is within the inductive field volume of the transmit coil).

Several wired or wireless input applications, including smart phone or tablet applications can also be used, wireless remote controls for example. These additional input applications can provide additional inputs to the system to adjust the therapy, adjust the closed loop algorithm, adjust stimulation outputs, adjust optimization or to adjust the algorithm mode as necessary. The input application can display electromyogram data for the user, allows the user to adjust the parameters that control the EMG collection, such as the input filters, trigger amplitudes, frequency ranges, etc.

An input application can also allow for automated therapy titration. In this mode, the application can run custom software that provides stimulation to a target site of the subject, such as a target nerve or target muscle and monitors the resulting evoked EMG activity of a muscle, such as an anterior lingual muscle, including the genioglossus muscle. The resulting EMG activity can correlate to the amount of airway opening desired (as inputted into the application) and thus can allow for automated therapeutic stimulation parameter settings and eliminate time consuming parameter adjustments during sleep Non-limiting example of stimulation parameter settings include stimulation pulse width, amplitude, frequency, electrode position/configuration and the like. In this aspect, the system can determine the therapeutic stimulation outputs and allows the subject/physician to fine tune as necessary. The subject or physician can rerun the automated parameter adjustment application at any time, and through the applications can be monitored remotely so that titration, programming can be done from the comfort of the subject's home.

The resultant evoked EMG signal can be continuously monitored and stimulation parameters needed to produce the required tongue motion for effective treatment can be determined, even if the response to a given set of stimulation parameters changes over time, effectively reducing the amount of testing required for initial programming as well as the need for ongoing follow-up testing. Also, issues with the therapy (e.g., stimulation according to certain stimulation parameter settings is not providing the tongue movement necessary to open the airway) can be identified and alerts can be generated for the patient and/or physician (this allows for quicker response and proactive management of the system).

Figure 11:
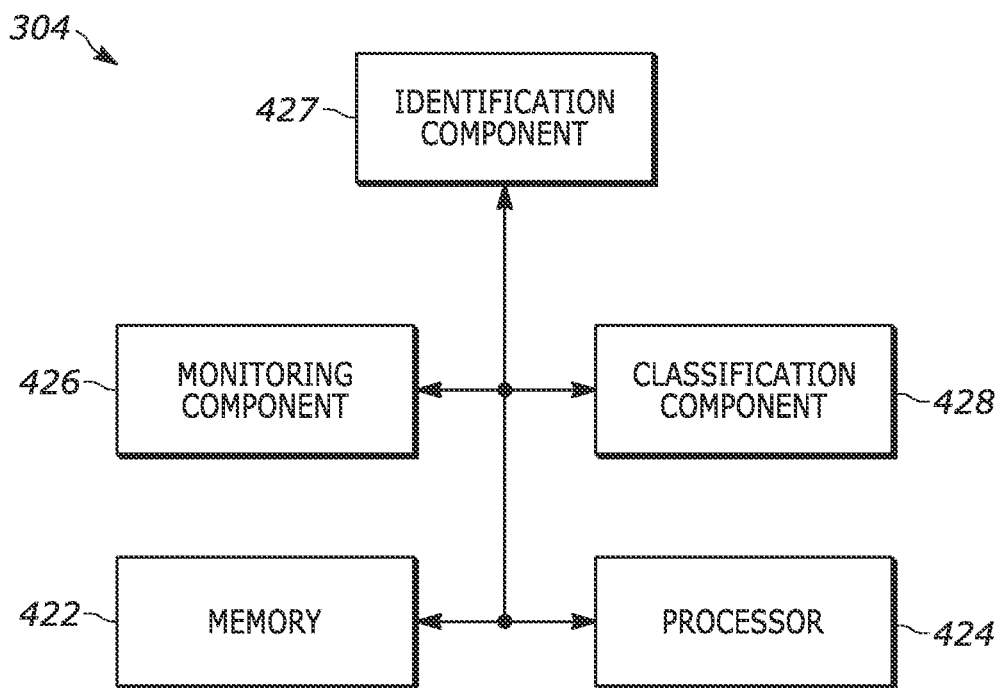
FIG. 11 is a block diagram of an example of the computing device shown in FIG. 11.
Figure 12:
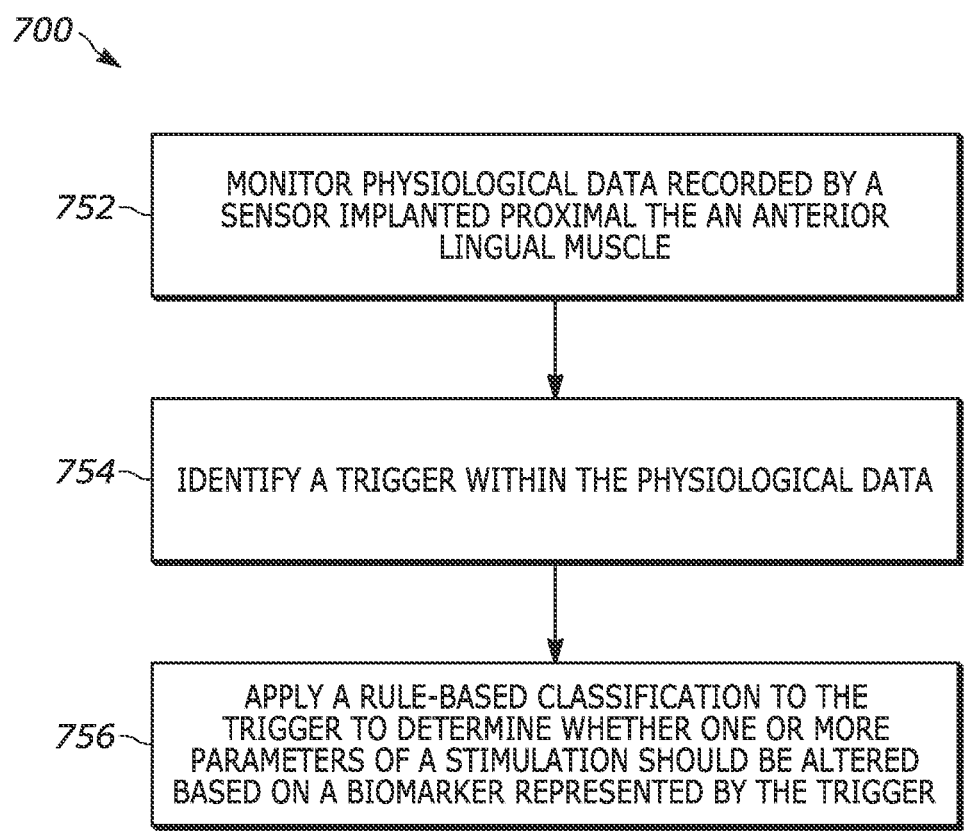
FIG. 12 is a process flow diagram of an example method for providing neural stimulation according to a closed loop algorithm to treat SDB, including OSA, according to an aspect of the present disclosure.

Another aspect of the present disclosure can include a method 700 (FIG. 11) for providing neural and/or muscular stimulation according to a closed loop algorithm to treat SDB. The method 700 can be executed by components of the systems as described and shown in the figures, for example. Portions of the method 700 can be stored at least in part on a non-transitory memory and executed by a processor.

For purposes of simplicity, the method 700 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 700 and/or more than the illustrated aspects may be required to implement the method 700. Additionally, one or more aspects of the method 700 can be stored in one or more non-transitory memory devices and executed by one or more hardware processors.

At 752, physiological data (e.g., related to inspiration, sleep stage and/or body position as indicated by an EMG, for example) recorded by one or more sensors can be monitored. The one or more sensors can be implanted adjacent to the anterior lingual muscle, such as the genioglossus muscle, or in the plane between the genioglossus muscle and geniohyoid muscle, for example. At 754, a trigger can be identified within the physiological data. The trigger be a change in at least one parameter of the physiological data (e.g., indicative of inspiration during respiration, body position, and/or a stage in the sleep cycle as indicated by an EMG, for example).

At 756, a rule-based classification can be applied to the trigger to determine whether one or more parameters of the stimulation should be altered based on a biomarker represented by the trigger. A signal comprising configuration/setting information for the parameters can be sent to one or more electrodes located adjacent to the hypoglossal nerve, for example. The stimulation parameter(s) can be titrated and adapted based on the trigger to optimize airway muscle tone.

Neuromodulation Device Configuration

Figure 2:
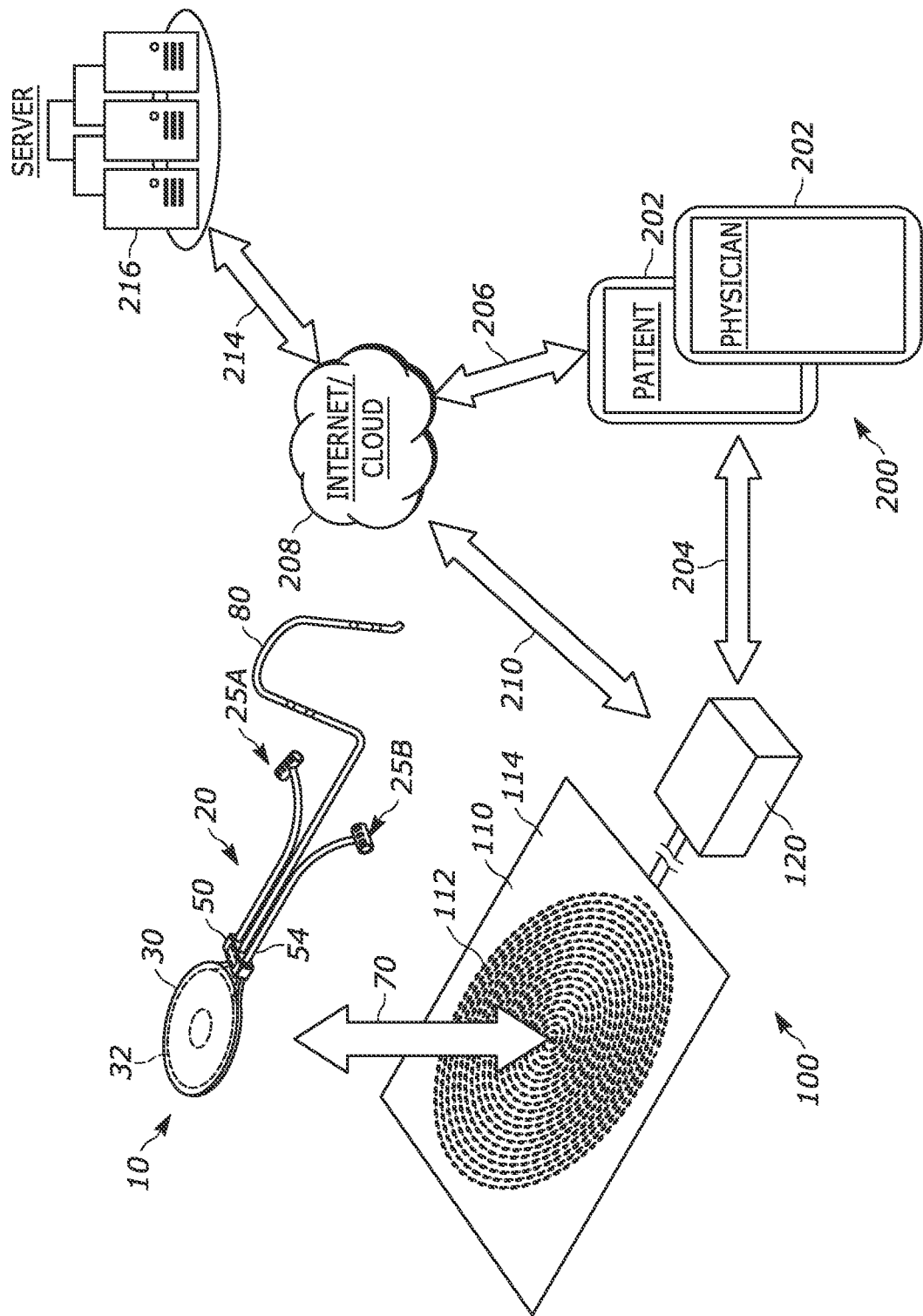
FIG. 2 is a schematic illustration of an implantable neuromodulation device of an implantable stimulation system according to an aspect of the present disclosure.

The neuromodulation device can have a variety of configurations, which can be tailored to the specific therapy being applied and/or to the anatomy at the site at which the stimulation therapy is applied. An example configuration of a neuromodulation device 20 is illustrated in FIG. 2. Neuromodulation device 20 can include a first stimulation lead 21A and a second stimulation lead 21B, each comprising a lead body 23 having a nerve cuff electrode 25 located thereon. The nerve cuff electrode 25 (enlarged in both FIGS. 1 and 2 for clarity) can comprise a cuff body 27 comprising a stimulating electrical contact 29 disposed thereon configured to deliver a stimulation signal to a target site. Although neuromodulation device 20 is illustrated as including two stimulation leads for stimulation of the left and the right hypoglossal nerve, for example, the neuromodulation device can include only one stimulation lead or more than two stimulation leads. Stimulating lead 21 can be generally elongated and include a plurality of electrodes 29 spaced along its length. The lead body can have different shapes. For example, the lead body can be cylindrical, flat or have an oval cross-sectional shape. The lead body can also have enlarged segments to allow for disposition of larger electrode pads or contacts thereon along the length of the lead body.

The stimulation leads as well as the nerve cuff electrodes can be configured to stimulate nerves bilaterally or unilaterally. The stimulation leads and nerve cuff electrodes can be configured to stimulate various combinations of nerves and nerve branches. Such nerves and nerve branches include the HGN (including a HGN nerve trunk, a medial branch of the HGN, a lateral branch of the HGN (as described in more detail below)); a glossopharyngeal nerve or other nerves that innervate a pharyngeal muscle; a lingual nerve; other nerves that innervate anterior lingual muscles; and/or other nerves that innervate the tongue.

The tongue receives afferent (sensory) innervation from branches emanating from four cranial nerves: a) trigeminal nerve, mainly the mandibular and lingual nerves, b) facial nerve, mainly the chorda tympani nerve, c) glossopharyngeal nerve and d) vagus nerve, mainly the superior laryngeal nerve. The efferent (motor) innervation of the tongue emanates from the hypoglossal nerve with small contribution form the cervical vagus nerve. The upper esophageal sphincter (otherwise called the cricopharyngeus muscle) has motor control through the glossopharyngeal nerve as well. Finally, innervation to the larynx originates from branches of the vagus nerve, the superior laryngeal nerve and recurrent laryngeal nerve.

The stimulation lead, which can be configured in many shapes, orientation and include one or more electrodes as needed to provide improved therapy, can be configured to stimulate any of these nerves and/or muscles bilaterally or unilaterally. The sensing lead can be configured to sense from different lingual muscles as to adopt a close loop control for therapy.

Further, although the second stimulating lead 21B is illustrated as having three stimulating electrical contacts 29b and first stimulating lead 21A is illustrated as having four stimulating electrical contacts 29a, the stimulating leads can have more or less stimulating electrical contacts. Each electrode 29 can be configured and utilized independently of the other electrodes. Because of this, all or some of electrodes 29, whichever is determined to be most effective for a particular implementation, can be utilized during the application of stimulation therapy.

Figure 3:
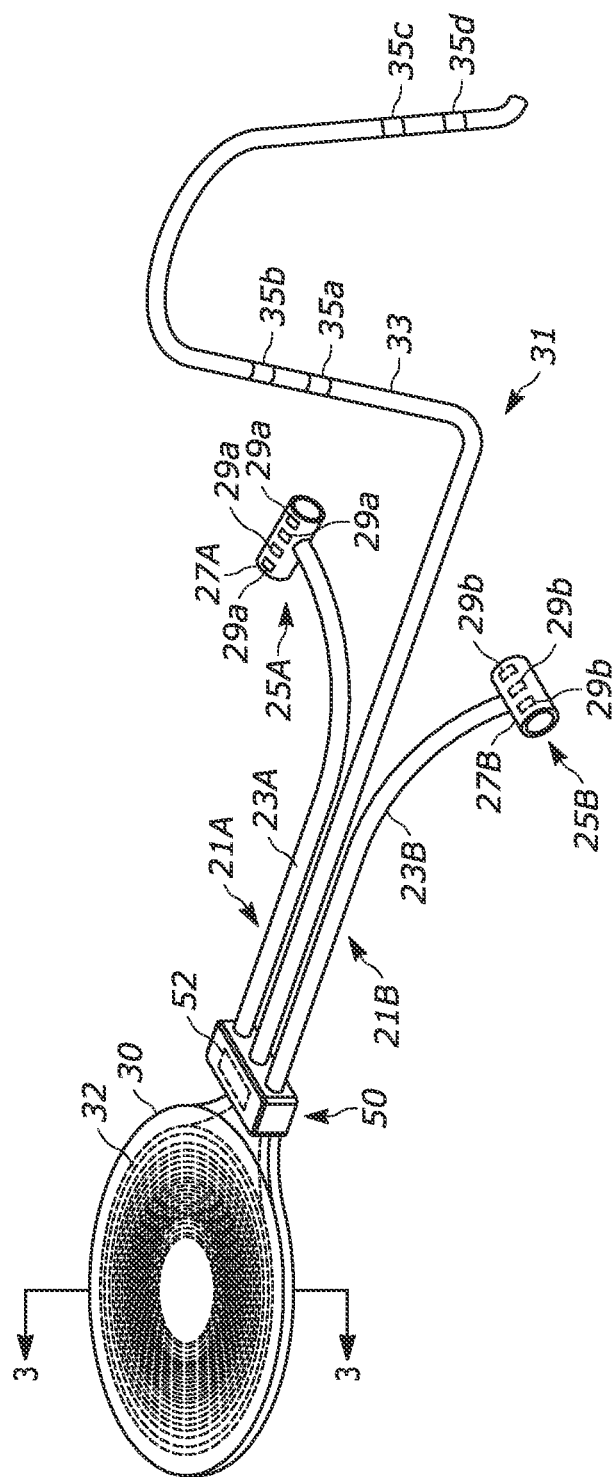
FIG. 3 is a schematic illustration of a neuromodulation device according to an aspect of the present disclosure.

Further, although FIG. 2 illustrates only one nerve cuff electrode located on the stimulating leads, the lead(s) can comprise more than one nerve cuff electrode. Referring to FIG. 3, a stimulating lead 53 can comprise a plurality of nerve cuff electrodes. For example, FIG. 3 (which mainly illustrates the nerve cuff electrodes of the lead) depicts stimulating lead 53 having a proximal cuff electrode 33 comprising a cuff body 51 having a stimulating electrical contact 37 disposed thereon. Proximal nerve cuff electrode 33 is sized and dimensioned to at least partially wrap around the circumference of a hypoglossal nerve trunk at or proximal to a branch point between a medial branch and a lateral branch of a hypoglossal nerve that innervates the genioglossus muscle. Stimulation lead 53 also includes a medial cuff electrode 39 comprising a cuff body 41 comprising a stimulating electrical contact 43 disposed thereon. Medial cuff electrode 39 is sized and dimensioned to at least partially wrap around the circumference of a medial branch of the hypoglossal nerve at or proximate to the branch point between the medial branch and the lateral branch of the hypoglossal nerve that innervates the genioglossus muscle. Stimulation lead 53 further includes a lateral cuff electrode 45 comprising a cuff body 47 comprising a stimulating electrode contact 49 disposed thereon. Lateral cuff electrode 45 is sized and dimensioned to at least partially wrap around the circumference of a lateral branch of the hypoglossal nerve at or proximate to the branch point between the medial branch and the lateral branch of the hypoglossal nerve that innervates the genioglossus muscle. The branch point referred to above is distal to the branch of the hypoglossal nerve that innervates the styloglossus and hyoglossus muscle and proximal to the distal most fibers of the hypoglossal nerve. The medial cuff electrode and the lateral cuff electrode can be sized and dimensioned to at least partially wrap around the circumference of the medial branch and the lateral branch of the hypoglossal nerve respectively at a location distal to the proximal cuff electrode. Although the proximal, medial and lateral nerve cuff electrodes are illustrates as being separate cuff electrodes, they can be an integral one-piece nerve cuff electrode. The nerve cuff electrode can collectively have a Y-shape. Each of the nerve cuff electrodes can comprise one to two stimulating electrical contacts, although they can also include more than two stimulating electrical contacts. In certain aspects, one or more of the nerve cuff electrodes comprises a plurality of electrodes arranged circumferentially about the respective cuff body spaced approximately 90 degrees apart. The stimulating electrical contacts can have various configurations such as a half-moon configuration arranged circumferentially about the respective cuff body. Again, as mentioned above, the nerve cuff electrodes can be configured to stimulate the hypoglossal nerve trunk, the lateral branch of the hypoglossal nerve, and/or the medial branch of the hypoglossal nerve either individually or in various combinations including in combination with stimulation of the glossopharyngeal nerve and/or lingual nerve.

It is well known in the art that one limitation of using cuff electrodes is the ability to selectively stimulation specific nerve fibers that produce the neurological function of interest when using a nerve cuff electrode on the main nerve trunk. This limitation can limit therapy and outcomes due to unwanted stimulation that causes side effects and discomfort. Therefore, applying stimulation via a nerve cuff on the main trunk of a nerve causes limitation in the therapy, however, using nerve cuff electrodes have advantages when placed on the right nerve or nerve branch to produce the stimulation of interest while minimizing side effects. Nerve cuff electrodes can reduce electrical current spread to structures outsides the nerve cuff, hence reducing side effects. Placing one or more nerve cuffs at specific nerve branches can provide direct stimulation to the nerve fibers of interest and allow for tailoring of the therapy by stimulating one or more nerve branches to produce improved stimulation for therapeutic outcomes that are meaningful to patients. The stimulation can be tailored by using specific levels of current at each of the one or more cuff electrodes on the nerve branches to cause the right outcomes for each patient. The nerve branching patterns can and are different patient to patient and hence the need to provide one or more cuff electrodes placed on specific branches and the system flexibility to provide specific amount of current to each cuff is advantageous to cause specific actions without unwanted side effects. Each of the one or more cuff electrodes, can have one or more electrodes that are sized, shaped and orientated to address the specific fibers within the nerve branch of interest and to stimulate those specific fibers for therapeutic outcomes. The electrodes within each cuff may not all be the same and can have different shapes and sizes to provide specific stimulation to each nerve branch. The size of the nerve branch and the types of fibers within the nerve branch can be important to the understanding of the stimulation and electrode configurations.

Figure 5:
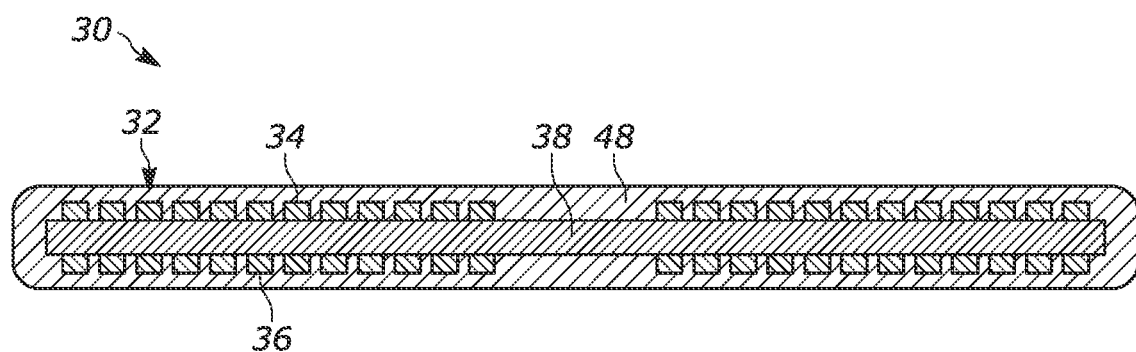
FIG. 5 is a section view taken generally along line 3-3 of FIG. 3, illustrating an antenna portion of the implantable neuromodulation device.

A neuromodulation lead can also include a sensing lead 81 comprising a lead body 83 having a sensor disposed thereon. The sensor is configured to record physiological data and can be, for example, an EMG electrode. FIG. 5 illustrates one 3-D shape to which a sensing lead 81 (as well as a stimulation lead) can be formed. The example configuration of FIG. 5 shows the sensing lead formed three-dimensionally in a generally omega-shape, as shown in the plan view of FIG. 5. This particular 3-D configuration can be implemented to position the sensing electrical contacts at different positions along the HGN and genioglossus muscle, where the neuromodulation device is configured to treat SDB, such as OSA, for example. More specifically, the configuration of the sensing lead in FIG. 5 can allow for the right and left electrical contacts (as viewed in FIG. 5) to be placed in very close proximity to the HGN branches and to provide slight cranial pressure to place the electrodes onto the surface of the genioglossus muscle, the largest of the tongue protrusion muscles. The right and left electrical contacts in an implanted configuration can extend along the posterior-anterior course of the HGN, placing the electrical contacts at or near the location of the branch points, such as distal branch points from the main trunk. Electromyography recording of the genioglossus muscle have shown that that the activity is more pronounced as the recordings progress to a more anterior positions on the genioglossus. By using this specific shape, the EMG recording using one or more electrodes can be modified as needed and moved to a more anterior location as needed to produce the best electrical signal characteristics. In addition, the electrodes configuration used for recording can be modified to capture unilateral EMG (one from both sides of the patient) which can be used to sense differences between the right and left side (or vice versa) during therapy or to naturally occurring differences that occur during different sleeping positions, which could be used by the system to direct therapy. Using this specific shape, that tracks the nerve branching patterns bilaterally and by applying an slight upward bias to each of the sections that house the electrodes allows for reduced signal to noise ratio in the recordings, reducing movement during use, and provides for stable recording over the duration of the implant.

In more detail, the sensing lead can be inserted and positioned in the plane between the geniohyoid muscle and the genioglossus muscle. The sensing lead can be configured to position sensing electrical contacts along the nerve distribution of the hypoglossal nerve and its branches bilaterally and configured to sense electrical information from the genioglossus muscle by applying a slight upward pressure against the dorsal surface of the genioglossus muscle with the 3D bias of the sensing lead when the electrode are placed. As depicted in FIG. 5, in an aspect, sensing lead 81 can comprise a lead body 83 having a left portion 55 comprising a left set of electrical contacts 57, a right portion 59 comprising a right set of electrical contacts 61, and an intermediate portion 63 therebetween defining an apex 65 of lead body 53. As described in more detail below, the sensing electrical contacts can be used to sense electrical activity, such as intrinsic or evoked electrical signals. FIG. 5 depicts two electrical contacts per side but the sensing lead can comprise more or less sensing electrical contacts. For example, the left and right portion of the lead body can each have one electrical contact and a common reference electrical contact can be located in the intermediate portion of the lead body for example.

Lead body 83 can be biased towards a substantially omega shape, more generally speaking a shape that allows for the two sections to extend from a center section, when fully deployed as shown in FIG. 5. In other words, lead body can be configured to transition from a substantially linear shape, in a non-deployed state, such as during insertion, to a substantially omega shape, as shown in FIG. 5, when fully deployed. When the sensing lead is in a non-deployed state, sensing electrodes 57 and 61 can be arranged in two groups of two electrical contacts spaced along the distal portion of lead body 83. One group of electrical contacts 61a and 61b can be positioned distally near an end of lead body 53 and one group 57a and 57b can be positioned proximally, between the distal group and electronics package (not shown in FIG. 5 but illustrated in FIG. 2). The configuration of electrical contacts 57 and 61 can, however, vary. The sensing lead can include a different number of electrical contacts, and/or the electrical contacts can be grouped, spaced, or otherwise arranged in different configurations along the length of the lead.

The sensing lead is fully deployed when the neuromodulation lead is implanted in the patient's body and the electrical contacts are positioned at the desired locations in the patient's body. The omega shape of the sensing lead can be created at the time of manufacturing such that the final form of the lead body is biased to have the omega shape, such bias being overcome if needed during insertion of the lead. The bias can be created, for example, by heat shaping or material shaping or other methods of manufacturing a biased lead.

The sensing electrical contacts can be ring electrical contacts extending substantially 360° about the lead body, for example, and can have substantially the same size as the target stimulation site(s). The sensing electrical contacts can also be directional electrodes and not extend 360° about the lead body. Further, the electrical contacts can have coatings to reduce the signal to noise ratio and/or allow for better long-term recording characteristics.

Intermediate portion 63 of lead body 83 can define an apex 65 and an ultrasound marker 67 can be disposed at apex 65. As such, the sensing lead can be inserted via ultrasound and ultrasound marker 67 can allow the user to identify when the apex of the sensing lead is positioned at midline, allowing the electrical contact sets 57 and 61 to be positioned along the distribution of the hypoglossal nerve and its branches bilaterally. Ultrasound can also be used to track motion or potential dislodgment of the lead over time. One or more anchors can be disposed on the lead body to secure the sensing lead in place. Such anchors can be hard or soft anchors, for example, including tines, barbs, prefabricated sutures, deployable anchors including time dependent deployable anchors (e.g. anchors that are polymer coated and deploy or release once the polymer dissolves), or combinations thereof.

Figure 6:
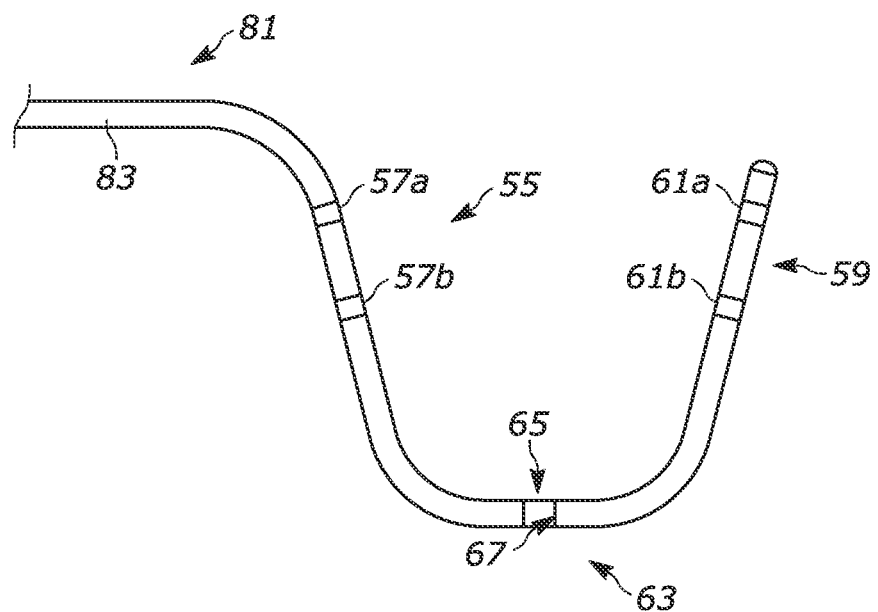
FIG. 6 is a schematic illustration depicting an exemplary configuration of a sensing lead or stimulation lead of a neuromodulation device according to an aspect of the present disclosure.

In certain aspects and with respect to FIG. 6, when sensing lead 69 (as well as a stimulation lead) is fully deployed, intermediate portion 71 of lead body 73 defining apex 75 can be located inferior/caudal/lower to the left and right electrode sets 77 and 79 respectively. This can be seen in the inferior bend or bias of lead body 73 that leads into intermediate portion 71. Such a bend or bias can allow the lead to exert upward/superior/cranial pressure to press the sensing electrodes against the genioglossal muscle and/or the hypoglossal nerve to allow for better contact between the electrode sets and the hypoglossal nerve and/or genioglossus muscle. In particular, this pressure is created by the intermediate portion, including the apex, being more caudal in the body and allowing the left and right portion of the lead body to be pushed more cranially into the genioglossus muscle. This bias allows for better contact with the genioglossus muscle, more lead stability and hence better long-term performance of the lead and allowing for a better signal to noise ratio for recording purposes.

In particular, such a bias can reduce motion of the lead after encapsulation/scar tissue grows around the lead and thus allow for better contact between sensing electrodes and the muscle(s) from which electrical activity is sensed. The inferior bias can also reduce the amount of encapsulating tissue around the lead as well. This can improve the recording of electromyography (EMG) signals from muscles innervated by the hypoglossal nerve since the more encapsulating tissue around the sensing electrodes, the harder it can be to detect an EMG signal long term. As such, reduced motion of the lead and less encapsulation of tissue around the lead can result in better EMG recording.

Referring back to FIG. 2, neuromodulation device 20 can include power receiver 30 and electronics package 50. Power receiver 30 can include a coiled receiver antenna 32 that is packaged in a protective biocompatible material and is operatively connected to the electronics package 50 and electronic components 52 mounted therein. The stimulating and sensing leads 21 and 31 can be operatively connected to the electronics package 50, which controls the operation of the stimulating electrical contacts 29 and sensing electrical contacts 35. Electrical contacts 29 and 35 can be electrically connected to electronics package 50 by conductors, such as wires. As stated above, electrical contacts 29 can be utilized as stimulating electrodes to apply stimulation to a target anatomical structure, such as, for example, a nerve or muscle. Sensing electrodes 35 can be used to detect and measure an EMG response, for example, from a neuromuscular structure associated with the target nerve. For a SDB treatment implementation illustrated in this description, the target nerve can be the HGN and the associated muscle can be the genioglossus muscle. The neuromodulation device can, however, be used to target other nerves and to measure physiological electrical signals from other anatomical structures, such as EMG responses, from other neuromuscular structures.

Electronic components 52 are preferably implemented in an application-specific integrated circuit (ASIC). The electronic components 52 can, however, include one or more ASICs, discrete electronic components, and electrical connectors for connecting the electronic components to power receiver 30 and/or leads 21 and 31. The electronic components, whether embodied in a single ASIC or one or more components, can, for example, include processing and memory components, e.g., microcomputers or computers-on-a-chip, charge storage devices (e.g., capacitors) for accumulating a charge and supplying stimulation power, and solid state switching devices for selecting the identities of the electrodes (e.g., anode, cathode, recording electrode) and modulating power supplied to the electrodes (e.g., pulse-width modulation (PWM) switches).

To provide comfort to the patient and ease of insertion for physicians, the neuromodulation device 20 can have a generally soft/flexible construction. This soft/flexible construction can apply to leads 21 and 31, power receiver 30, or both the leads and the power receiver. In one example configuration, the neuromodulation device components—power receiver 30, electronics package 50, and leads 21 and 31—can be coated or otherwise encased simultaneously in a single operation, such as an insert molding with a biocompatible material, such as silicone, epoxy, and various suitable polymers.

The power receiver and the leads can have a flexible configuration that allows either or both structures to bend or flex, which facilitates implantation compatibility with a variety of anatomical structures. The power receiver can be generally flat and planar in configuration and the stimulation and sensing leads can be generally elongated in configuration in a non-deployed configuration and can extend axially from the electronics package. To facilitate the flexible configuration of the leads, the stimulating and sensing electrical contacts and the conductors that connect the sensing and stimulating electrical contacts to the electronics package can be encased and supported in a covering. The covering can be formed of a biocompatible material, such as silicone and various suitable polymers, and can be configured to leave exposed the stimulating and sensing electrical contacts or portions thereof. The covering can be formed, for example, in the aforementioned insert molded covering of the neuromodulation device.

To facilitate the flexible configuration of power receiver 30, antenna 32 can be formed on a soft substrate so as to be flexible and conform to the anatomy at the site of implantation. For example, power receiver 30 can have a flexible printed circuit board (PCB) construction in which antenna 32 is etched from a thin layer of conductive metal laminated on a substrate 38 (see FIG. 4) constructed of a flexible material, such as a polymer. In one particular flexible PCB construction, the substrate can be a polyimide material and the conductive metal can be copper. Other flexible PCB constructions can be implemented. Antenna 32 can be encased and supported in covering 48. Covering 48 can be formed of a biocompatible material, such as silicone, epoxy and various suitable polymers. Covering 48 can be formed, for example, in the aforementioned insert molded covering of the entire neuromodulation device 20 structure.

The flexible PCB of power receiver 30 can extend into electronics package 50 and can be configured to mount the electronic components 52. The PCB can also be configured to interface conductors of the leads, and/or to form portions of the lead itself. In this instance, power receiver 30, electronics package 50, and leads 21 and 31 (or portions thereof) can be encased in the biocompatible material (e.g., silicone, epoxy and various suitable polymers) simultaneously.

The power receiver is designed with the goal of delivering maximum power to the neuromodulation device from a given external magnetic field. With this goal in mind, for the HGN stimulation implementation of the example configuration disclosed herein, power receiver 30 and receiving antenna 32 have a unique configuration designed to adhere to several criteria for neuromodulation device 20. The criteria depend, of course, on the intended therapeutic use of the system and the configuration resulting therefrom. The criteria set forth below are specific to an example configuration of system 10 for treating SDB including OSA via neuromodulation of the HGN:

The neuromodulation device 20 operates within the guidelines for maximum permissible magnetic field exposure as recommended in IEEE Standard C95.1-2005 (Reference 3).

The receiving antenna 32 allows for near continuous power consumption (10-30 milliwatts (mW)) from the neuromodulation device 20.

The receiving antenna operates at a frequency ranging from 100 kHz to 2.4 GHz ISM (industrial, scientific, medical band of the radiofrequency spectrum). In one particular implementation, frequencies of 6.78 MHz or 13.56 MHz were used.

The receiving antenna 32 has a diameter of 2-3 cm. and be as thin as possible to maintain flexibility.

The neuromodulation device 20 is small enough for minimally invasive subcutaneous implantation within the soft tissue of the sub-maxillary neck.

The neuromodulation device 20 maintains a soft, flexible design so that it can be manipulated to conform to the anatomy of the patient.

Other stimulation therapies or implementations of the implantable stimulation system 10 can cause some or all of these criteria to be changed or adjusted, and also for certain criteria to be added or removed.

Figure 4:
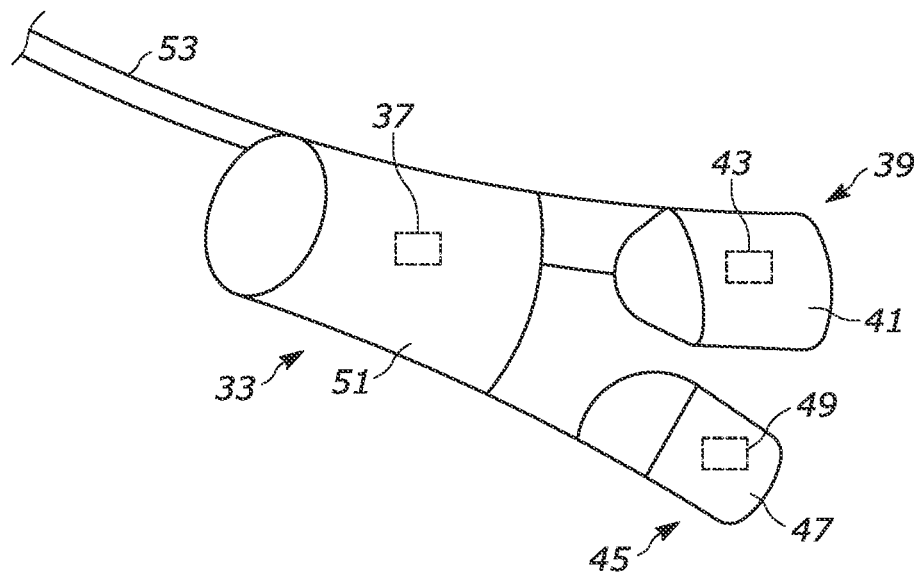
FIG. 4. is a schematic illustration of a portion of a neuromodulation device according to an aspect of the present disclosure.

To meet these criteria, receiving antenna 32 can have a double-layer, flat, "pancake" configuration. Referring to FIG. 4, antenna 32 can have a flexible PCB construction in which first or upper/top antenna coil 34 is formed on a first or upper/top side of substrate 38 and second or lower/bottom antenna coil 36 is formed on a second or lower/bottom side of the substrate. Substrate 38 can be a thin (e.g., 1 to 3 mil) polyimide layer and coils 34, 36 can be etched from thin layers of copper or gold (e.g., 1 oz./ft$^2 \approx$ 1.4 mil) laminated onto substrate 38.

PCB 38 can also support electronic components 52 in electronics package 50. Using guidelines for maximum permissible magnetic field exposure, IEEE Standard C95.1-2005 (which is incorporated herein by reference in its entirety), the maximum achievable delivered power is approximately 10-30 mW at 6.78 MHz frequency. These power requirements were chosen based on the estimated requirements for components 52 of electronics package 50, the estimated maximum stimulation parameters, and pre-clinical studies, while also including a safety factor to allow for capacitor charging and to provide transitional power. Transitional power can be provided via a variety of components, such as capacitors, supercapacitors, ultracapacitors, or even a rechargeable power source, such as a battery. Continuous power during patient movement, especially at the high end of power ratios and/or when coupling is not ideal. The transitional power source helps ensure complete, continuous operation of the neuromodulation device 20, even during patient movement.

Those skilled in the art will appreciate that, in operation, an antenna can be susceptible to power losses due to substrate losses and parasitic capacitance between coils 34, 36 and between the individual coil turns. Substrate losses occur due to eddy currents in the substrate due to the non-zero resistance of the substrate material. Parasitic capacitance occurs when these adjacent components are at different voltages, creating an electric field that results in a stored charge. All circuit elements possess this internal capacitance, which can cause their behavior to depart from that of "ideal" circuit elements.

Advantageously, antenna 32 can implement a unique two-layer, pancake style coil configuration in which coils 34, 36 are configured in parallel. As a result, coils 34, 36 can generate an equal or substantially equal induced voltage potential when subjected to an electromagnetic field. This can help to equalize the voltage of coils 34, 36 during use, and has been shown to significantly reduce the parasitic capacitance of antenna 32. In this parallel coil configuration of antenna 32, top and bottom coils 34, 36 are shorted together within each turn. This design has been found to retain the benefit of lower series resistance in a two-layer design while, at the same time, greatly reducing the parasitic capacitance and producing a high maximum power output.

Figure 7:
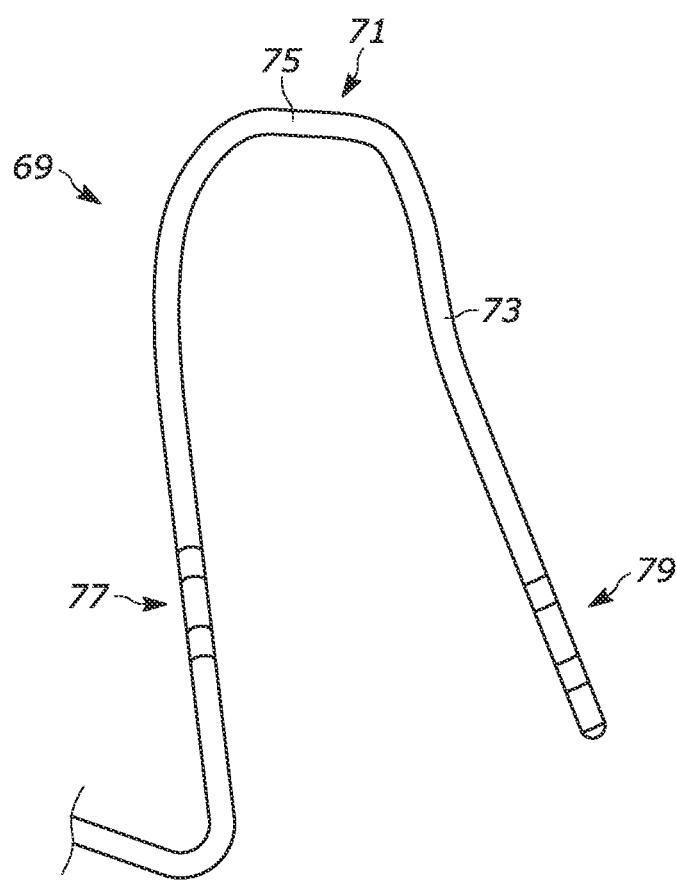
FIG. 7 is a schematic illustration depicting an exemplary configuration of a sensing lead or stimulation lead of aneuromodulation device according to an aspect of the present disclosure.

This improved, parallel configuration of antenna 32 is illustrated in FIGS. 7A and 7B, which illustrate the top and bottom coils 34 and 36, respectively, on PCB substrate 38. Each coil 34, 36 can include a plurality of coil windings or turns 40 and can be characterized by the following properties: number of turns (N), outside diameter (OD), coil pitch (P), trace width (W), trace thickness (T), and coil spacing (S). These properties are measured as follows:

The OD is the diameter of coil 34, 36 measured across the coil between outer edges of outermost turn 40.

The coil pitch P is the spacing between turns 40 measured between any two adjacent turns.

The coil width W is the width of each coil turn 40.

The trace thickness T is the thickness of turns 40, which is determined by the thickness of the conductive (Cu) layers laminated onto substrate 38 in the PCB construction.

The coil spacing S is the distance between coils 34, 36, which is determined by the thickness of substrate 38 in the PCB construction.

In one particular configuration of antenna 32, PCB substrate 38 is a 2 mil polyimide layer and coils 34, 36 are etched from 1.4 mil copper laminated onto the substrate. The parallel coil configuration of the antenna 32 results from electrically connecting the turns 40 of the coils 34, 36 through substrate 38. These connections can be in the form of electrically conductive connectors illustrated at 42 in FIGS. 9A and 9B. Connectors 42 between the turns 40 can, for example, be formed by drilling or laser etching holes through the PCB structure, e.g., through substrate 38 and turns 40 of the upper and lower coils 34, 36, and plating or filling the holes with a metal, such as plated copper/gold or melted and/or flowed tin-lead, for example, to electrically connect the turns on the opposite surfaces of the substrate. The connectors could also be formed mechanically, e.g., pins or rivets.

Coils 34, 36 of antenna 32 have a unique configuration that allows for their parallel interconnection. On each side of antenna 32, turns 40 are semi-circular, each having a fixed diameter with closely spaced ends. This is opposed to a traditional coil configuration in which the diameter of the turns varies continuously in a spiral that decreases progressively from outside to inside. To create the coiled configuration of the antenna 32, on one side of the antenna (upper coil 34 side in the example configuration of FIG. 7A), links 44 can extend diagonally between adjacent turns 40 of upper coil 34. Links 44 can be formed as portions of the copper layer, for example, laminated onto substrate 38, and therefore can be formed coextensively with turns 40 of upper coil 34 as one continuous conductive (Cu) strip. Upper coil 34 can therefore be configured as a continuous coil having decreasing diameter from outside to inside and can therefore function as a spirally configured coil.

On the lower coil 36 side of antenna 32, turns 40 can also be semi-circular, each having a fixed diameter with closely spaced ends. There can be no links connecting adjacent turns 40 of lower coil 36. Instead, on the lower coil 36 side of antenna 32, terminals 46 can be formed—one connected to a terminal end of the innermost turn of the lower coil, and one connected to a terminal end of the outermost turn of the lower coil. Terminals 46 can be connected to innermost turn 40 and can extend in the space between the ends of the remaining turns.

Viewing FIGS. 7A and 7B, turns 40 of upper and lower coils 34, 36 can be interconnected at each of connectors 42.

Through connectors 42, the links 44 interconnecting the adjacent turns 40 of the upper coil 34 can also interconnect the adjacent turns of lower coil 36. Thus, turns 40 of the lower coil 36 also can be arranged in a continuous coiled configuration through connectors 42 and links 44. Lower coil 36 therefore can be configured as a continuous coil having decreasing diameter from outside to inside and can therefore function as a spirally configured coil.

Terminals 46 can be electrically connected to both upper coil 34 and lower coil 36 through connectors 42. The terminal ends from which terminals 46 extend can be radially opposite ends of inner and outer turns 40. As shown, terminal 46 of innermost turn 40 is connected to a first end of the turn, on a first side of the space between the opposite ends of the turns; whereas the terminal of outermost turn 40 is connected to an opposite second end of the turn, on an opposite second side of the space between the opposite ends of the turns.

For the configuration illustrated in FIGS. 7A and 7B, the performance of the antenna can depend on the properties listed above. Example configurations of the antenna, for which some of these properties were adjusted, were tested. These example configurations are illustrated in the following table:

| Property | Example 1 | Example 2 | Example 3 | Example 4 |
|---|---|---|---|---|
| Outer Diameter (OD) | 30 mm | 30 mm | 30 mm | 26 mm |
| # Turns (N) | 12 | 10 | 8 | 10 |
| Coil Pitch (P) | 1.0 mm | 1.0 mm | 1.0 mm | 1.0 mm |
| Trace Width (W) | 0.5 mm | 0.5 mm | 0.5 mm | 0.5 mm |
| Trace Thickness (T) | 1.4 mil | 1.4 mil | 1.4 mil | 1.4 mil |
| Coil Spacing (S) | 2 mil | 2 mil | 2 mil | 2 mil |
| Max. Power Delivery | 32.0 mW | 39.4 mW | 43.7 mW | 23.3 mW |

As shown in the above table, the maximum power delivered provided by each example coil configuration met or exceeded the 10-30 mW power requirement, even with the reduced coil outside diameter of Example 4.

The external controller 100 can have two components: power mat 110 and bedside control unit 120. Control unit 120 can be connected to power mat 110 by wire, for example, and is designed to be placed bedside, e.g., on a nightstand. The control unit can include a user interface, e.g., buttons, knobs, touchscreen, etc., to allow the user to control operation of the system when using the system in bed. Power mat 110 can be designed to be placed on the sleeping surface, such as a bed mattress, and therefore can be configured to have the form of a pad, e.g., a thin, flat, soft, flexible and non-slip configuration. Power mat 110 supports one or more wireless power transmit coils 112 in or on a flexible or semi-flexible surface 114. Power mat 110 can be positioned on the sleeping surface so that a lower edge 116 of the mat corresponds approximately to the position of the patient's shoulders while sleeping. The shape and size of the power mat 110 can correspond, for example, to that of a pillow, such as a queen size pillow.

Control unit 120 can excite power transmit coils 112 to generate an electromagnetic field. External controller 100 can utilize transmit coils 112 in power mat 110 to provide tethered wireless power transfer to neuromodulation device 20 by way of receiving antenna 32 through electromagnetic induction. When the patient is in the sleeping position on the sleeping surface, antenna 32 of neuromodulation device 20 can be positioned within the electromagnetic field produced by transmit coils 112 of power mat 110. The shape of the field can be tailored through the configuration of the coils 112 to provide a field that is optimized for powering the neuromodulation device 20 through various sleeping positions. For example, the field can be configured extend horizontally (as viewed in FIGS. 8A-C) between the coils 112, so that the neuromodulation device 20 can be powered any time it is positioned within the vertical bounds of the horizontally extending field.

Through induction, electric current can be induced in receiving antenna 32 and that current can be provided to neuromodulation device electronics package 50. Components 52 in electronics package 50 control the operation of the electrical contacts. Through this operation, electrical contacts 29 can be utilized as stimulating electrodes for applying electrical stimulation to nerves or muscles, for example and electrical contacts 35 can be used as EMG sensing electrodes, for example, for detecting a neuromuscular response, to the application of electrical stimulation.

In addition to providing power to neuromodulation device 20, external controller 100 can also provide a data link for facilitating two-way communication between the controller and the neuromodulation device. While powering the neuromodulation device, controller 100 can simultaneously provide a wireless data signal that is used to program the neuromodulation device with settings, such stimulation parameters, and also retrieve stored data from the neuromodulation device, such as triggered stimulation events, measured EMG responses or other electrical physiological signals, current values, electrode impedances, and data related to the wireless power transfer between controller 100 and neuromodulation device 20.

Additionally, the neuromodulation device 20 can monitor the impedance and/or voltage of the neuromodulation device antenna 32 so that the power supplied to the neuromodulation device can be calculated. This can be provided as feedback to the controller 100 that allows the controller to adjust the current supplied to the power transmit coils 112. The controller 100 can control the power delivered to the neuromodulation device so as to remain within the standards/requirements set forth above. At the same time, the feedback can also facilitate increasing the current supplied to the power transmit coils 112 so that adequate power transfer to the neuromodulation device 20 is maintained, again within the prescribed limits. In this manner, the controller 100 can implement closed-loop control to optimize the power supplied to the neuromodulation device 20.

The operation of the controller 100 can be controlled through the user interface 200, which allows the user, e.g., the patient, physician or other caretaker, to control aspects of the operation of the implantable stimulation system 10. The control can be local, e.g., by the patient using a user interface of the control unit 120 or the patient user interface 200, or remote, e.g., by the physician through internet/cloud 208. The control unit 120 can have a small footprint and power mat 110 can be flexible in design so that external controller 100 is small, discreet, and portable for travel purposes.

Power Mat Configuration

To account for varying sleeping positions throughout the night, power mat 110 can have a large enough footprint to allow patient movement while still maintaining the ability to transmit power to neuromodulation device 20. At the same time, external controller 100 does produce electromagnetic radiation at a level that falls outside the guidelines for maximum permissible magnetic field exposure as recommended in IEEE Standard C95.1-2005 (Reference 3).

Figure 8A:
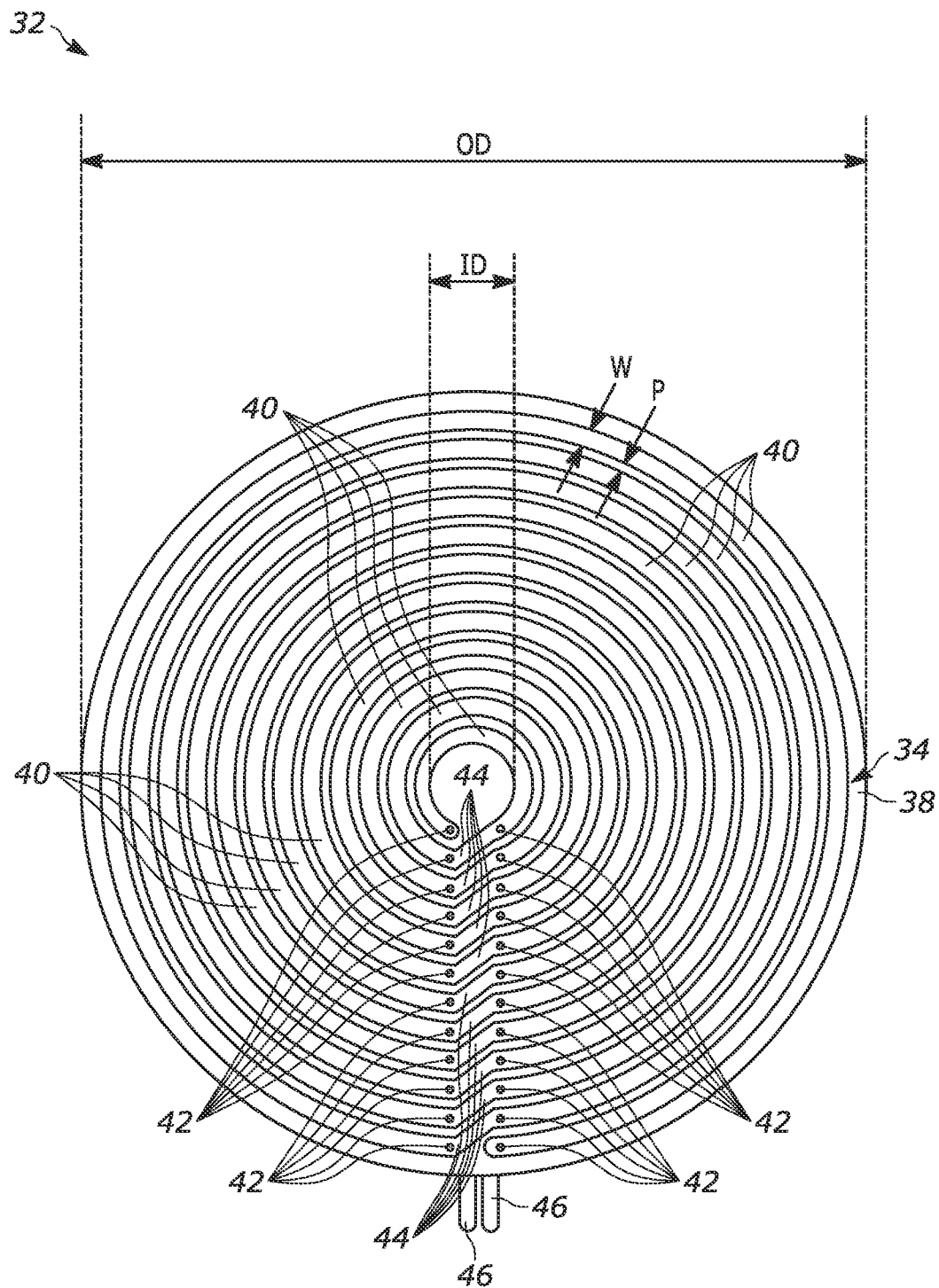
FIGS. 8A-8B are schematic illustrations depicting an exemplary configuration of an antenna portion of a neuromodulation device according to an aspect of the present disclosure.
Figure 8B:
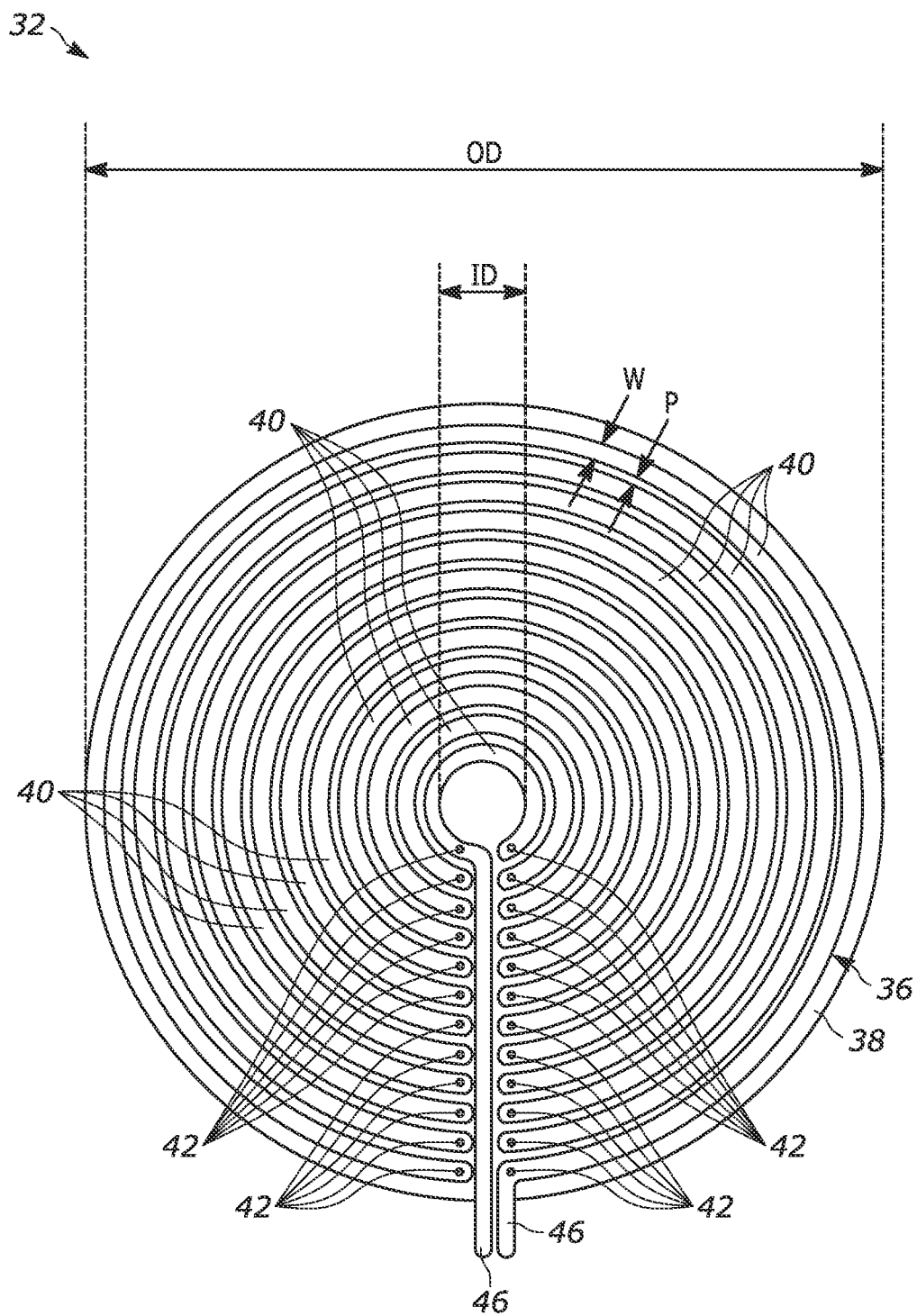

Example transmit coil configurations that can be implemented in power mat 110 are illustrated in FIGS. 8A-8C. These example transmit coil configurations can be implemented with a flex circuit design, i.e., the coils can be formed (e.g., etched) from a conductive metal (e.g., copper or gold) laminated on a flexible substrate (e.g., polyimide). The examples of FIGS. 8A-8C illustrate the overall shape of transmit coils 112 without showing the individual turns of the transmit coils. This is because the properties of the transmit coils 112, e.g., the number of turns, coil pitch/spacing, trace width, etc. is not limited, as can be the case with coils 34, 36 of antenna 32. Antenna coils 34, 36 can be tailored specifically for maximum induced power generation due to the small footprint limitations of antenna 32 of neuromodulation device 20. Power mat 110 can be larger in comparison and transmit coils 112 can be free to be configured to produce a magnetic field that can be limited only by requiring a level that falls within the IEEE magnetic field exposure guidelines mentioned previously.

Accordingly, transmit coils 112 can be configured to maximize the space or volume that the magnetic field covers so as to allow for variations in the patient position during sleep. This can give the system the ability to continuously power the neuromodulation device through a variety of sleeping positions throughout the night. FIG. 8A shows a twelve coil example configuration of transmit coils 112; FIG. 8B shows a two coil example configuration of transmit coils; and FIG. 8C shows a four coil example configuration of transmit coils. For all of these example configurations, experimental testing showed that transmit coils 112 are capable of meeting the system power requirements, within the IEEE exposure guidelines, while allowing for consistent power transfer to the antenna 32 over an effective volume of approximately 32×76×25 cm (L×W×H), which was found to be sufficient to cover the patient during a normal sleep cycle.

The twelve coil configuration of transmit coils 112 in FIG. 8A can allow for dynamic control of the magnetic field produced by the power mat 110. Through data coupling and communication between external controller 100 with neuromodulation device 20, a determination can be made as to which coil(s) of the twelve coil configuration are effectuating the power coupling between the external controller and the neuromodulation device. Through this determination, the external controller 100 can power only those coils necessary to power neuromodulation device 20, given the current position of the patient relative to power mat 110. As the patient changes positions, the neuromodulation device can detect any decrease in power transmission, which can trigger a reassessment and the selection of different coil(s). This configuration can thus be self-tuning, on-the-fly to maximize the electromagnetic field produced by the power mat 110 in the area of the antenna 32.

The two coil configuration of the transmit coils 112 in FIG. 8B can be static power coils that produce a continuous electromagnetic field around power mat 110. This configuration can be tuned to maximize the electromagnetic field strength in the largest possible volume so that power transmission is maximized throughout a wide variety of patient positions.

In the example configurations of both FIG. 8A and FIG. 8B, power mat 110 can have a flexible construction facilitated by a flexible circuit construction of transmit coils 112 housed within a flexible cover, such as, for example, soft plastic, rubber, fabric, etc. Transmit coils 112 can, for example, have a flexible PCB construction similar to antenna 32 of neuromodulation device 20. For instance, transmit coils 112 can be constructed as a single layer flexible PCB, with conductive traces etched from copper, for example, laminated on a polyimide, for example, substrate.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Furthermore, all references cited herein are incorporated by reference in their entirety.

What is claimed is:

1. A neuromodulation system comprising:
an antenna configured to produce an induced current in response to being disposed in an electromagnetic field;
a stimulation lead extending from a proximal end at the antenna to a free distal end, the stimulation lead having a stimulating electrical contact disposed thereon and configured to be implanted adjacent to a stimulation site between a geniohyoid muscle of a patient and a genioglossus muscle of the patient, the stimulating electrical contact being configured to deliver a stimulation signal to either a right hypoglossal nerve of the patient or a left hypoglossal nerve of the patient;
a sensing lead comprising a sensing lead body extending from a proximal end at the antenna to a free distal end, the sensing lead body comprising a proximal portion and a distal portion, the proximal portion extending between the proximal end of the sensing lead body and the distal portion and the distal portion comprising a left region, a right region, and an intermediate region therebetween, the left region having a left sensing contact disposed thereon and the right region having a right sensing contact disposed thereon, wherein the distal portion of the sensing lead body is configured to be implanted between the genioglossus muscle and the geniohyoid muscle and adjacent to a sensing site such that the left sensing contact is positioned at a left side of the genioglossus muscle and the right sensing contact is positioned at a right side of the genioglossus muscle, the left and right sensing contacts being configured to record physiological signals from the sensing site, wherein the intermediate region comprises a bend that positions the intermediate region in a different plane than the left and right regions such that when the distal portion of the sensing lead body is placed between the geniohyoid muscle and the genioglossus muscle, the intermediate region is inferior of the left and right regions and pushes the left sensing contact and the right sensing contact cranially into the genioglossus muscle;
an electronics assembly comprising electrical components to generate the stimulation signal and to control the application of the stimulation signal via the stimulating electrical contact of the stimulation lead and sensing of the physiological signals via the left and right sensing contacts;
an external controller comprising a control unit and a power transducer that supports a power transmission coil that is excitable to produce the electromagnetic field for inducing electrical current in the antenna to power the electronics assembly; and
an internal computing device comprising:
a non-transitory memory storing instructions; and
a processor to access the non-transitory memory and execute the instructions to at least:
monitor the physiological signals recorded by the left and right sensing contacts;
identify a trigger within the physiological signals, wherein the trigger is identified as a biomarker for a condition related to sleep; and
apply a rule-based classification to the trigger to determine whether one or more parameters of the stimulation signal should be altered based on the biomarker and to alter the one or more parameters of the stimulation signal in response to the biomarker.

2. The neuromodulation system of claim 1, wherein the stimulation lead is a first stimulation lead and the stimulating electrical contact is a first stimulating electrical contact, the system further comprising a second stimulation lead extending from a proximal end at the antenna to a free distal end, the second stimulation lead having a second stimulating electrical contact disposed thereon and configured to be implanted adjacent to a second stimulation site between a geniohyoid muscle of the patient and a genioglossus muscle of the patient, the second stimulating electrical contact being configured to deliver a second stimulation signal to the other of the right hypoglossal nerve or the left hypoglossal nerve.

3. The neuromodulation system of claim 2, wherein:
the first stimulation lead has a first cuff body comprising the first stimulating electrical contact disposed thereon;
the second stimulation lead has a second cuff body comprising the second stimulating electrical contact disposed thereon; and
the sensing lead comprises a plurality of sensing contacts disposed thereon.

4. The neuromodulation system of claim 1, wherein the stimulation lead comprises:
a first cuff body sized and configured to at least partially wrap around a first nerve branch site comprising a hypoglossal nerve branch distal to a hypoglossal nerve trunk of the either of the right hypoglossal nerve of the patient or the left hypoglossal nerve of the patient; and
a second cuff body sized and configured to at least partially wrap around a second nerve branch site proximal to the first nerve branch site.

5. The neuromodulation system of claim 1, wherein the stimulation lead and the sensing lead are operably coupled to the electronics assembly and the electronics assembly is operably coupled to the antenna, the antenna configured to supply the induced electrical current to the electronics assembly to power the electronics assembly.

6. The neuromodulation system of claim 5, wherein the stimulation lead, the sensing lead, the electronics assembly, and the antenna form a single neuromodulation device, the antenna located at a proximal end of the neuromodulation device, the electronics assembly operably coupled to the antenna, and the stimulation lead and sensing lead extending distally away from the electronics assembly.

7. The neuromodulation system of claim 1, wherein:
the intermediate region defines an apex of the sensing lead body; and
the sensing lead body is biased towards an omega shape when the sensing lead is fully deployed within the patient and the intermediate region of the sensing lead body is biased towards an inferior position relative to the left and right regions when the sensing lead is fully deployed.

8. The neuromodulation system of claim 1, wherein the power transducer is a mat configured to be positioned between a sleeping surface and the patient.

9. The neuromodulation system of claim 1, wherein the antenna comprises an upper coil and a lower coil electrically connected to each other in parallel.

10. The neuromodulation system of claim 1, wherein the left and right sensing contacts are EMG sensors and the physiological signals are obtained from EMG activity from the genioglossus muscle.

11. The neuromodulation system of claim 1, wherein rules of the rule-based classification are adaptive.

12. The neuromodulation system of claim 1, wherein the trigger indicates a change in phasic and/or tonic genioglossus muscle activity during respiration.

13. The neuromodulation system of claim 1, further comprising a connector having a proximal end and a distal end, the antenna being electrically coupled to the stimulation lead and the sensing lead via the connector, and wherein the distal end of the connector is coupled to the proximal end of the sensing lead body.

14. A method of improving sleep disordered breathing in a patient suffering therefrom comprising:
providing the neuromodulation system of claim 1;
placing the stimulating electrical contact adjacent to theft stimulation site between the geniohyoid muscle of the patient and the genioglossus muscle of the patient, the stimulation site comprising a nerve trunk of the right hypoglossal nerve of the patient or the left hypoglossal nerve of the patient, a lateral branch of the right hypoglossal nerve of the patient or the left hypoglossal nerve of the patient, a medial branch of the right hypoglossal nerve of the patient or the left hypoglossal nerve of the patient, or suitable combinations thereof;
placing the distal portion of the sensing lead body adjacent to the sensing site such that the left sensing contact is positioned at the left side of the genioglossus muscle and the right sensing contact is positioned at the right side of the genioglossus muscle;
activating the left sensing contact and the right sensing contact to record the physiological signals from the sensing site; and
activating the stimulating electrical contact to deliver the stimulation signal to either the right hypoglossal nerve of the patient or the left hypoglossal nerve of the patient based on the recorded physiological signals to improve the patient's sleep disordered breathing.

* * * * *

UNITED STATES PATENT AND TRADEMARK OFFICE
CERTIFICATE OF CORRECTION

PATENT NO. : 11,691,010 B2
APPLICATION NO. : 17/147886
DATED : July 4, 2023
INVENTOR(S) : Caparso et al.

It is certified that error appears in the above-identified patent and that said Letters Patent is hereby corrected as shown below:

In the Claims

In Column 28, in Claim 14, Line 36, delete "theft" and insert -- the --, therefor.

Signed and Sealed this
Eighth Day of August, 2023

Katherine Kelly Vidal
*Director of the United States Patent and Trademark Office*